United States Patent [19]
Alves et al.

[11] Patent Number: 5,935,578
[45] Date of Patent: Aug. 10, 1999

[54] CONTRACEPTIVE VACCINE

[75] Inventors: Kenneth Alves, Manalapan; Sunil K. Gupta, Piscataway, both of N.J.; Gregory Franklin Hollis, Wilmington, Del.

[73] Assignee: Merck & Co., Inc., Rahway, N.J.

[21] Appl. No.: 08/765,243

[22] PCT Filed: Jun. 6, 1995

[86] PCT No.: PCT/US95/07295

§ 371 Date: Dec. 19, 1996

§ 102(e) Date: Dec. 19, 1996

[87] PCT Pub. No.: WO95/35118

PCT Pub. Date: Dec. 28, 1995

Related U.S. Application Data

[63] Continuation-in-part of application No. 08/264,101, Jun. 20, 1994, Pat. No. 5,693,496.

[51] Int. Cl.$^6$ .................................................. A61K 39/00
[52] U.S. Cl. ..................................... 424/185.1; 424/184.1; 530/350; 530/397; 514/843
[58] Field of Search ..................................... 530/350, 397; 424/184.1, 185.1; 514/843; 536/23.5

[56] References Cited

U.S. PATENT DOCUMENTS 4,879,213 11/1989 Fox et al. .

FOREIGN PATENT DOCUMENTS

93/25233 11/1993 WIPO .

OTHER PUBLICATIONS

Bowie et al. Science 247:1306–1310, Mar. 1990.

Kumar et al. PNAS 87:1337–1341, Feb. 1990.

Blobel et al. nature 356:248–252, Mar. 1992.

Lazar et al. Mol. Cell Biol. 8(3):1247–52, Mar. 1988.

Burgess et al. J. Cell Biol. 111:2129–38, Nov. 1990.

J.A. Parsons et al. (Ed.) "Peptide Hormones", published by University Park Press, see Chapter 1 by Rudinger et al., see pp. 1–6, Jun. 1976.

Reeck et al. Cell 50:667, Aug. 1987.

*Primary Examiner*—Anthony C. Caputa
*Assistant Examiner*—Heather A. Bakalyar
*Attorney, Agent, or Firm*—Kenneth R. Walton; Melvin Winokur

[57] ABSTRACT

The instant invention is drawn to a sperm surface protein in substantially pure form selected from a human PH30 beta chain protein and a mouse PH30 beta chain proteins. Such proteins are useful as contraceptive vaccines in humans and mice respectively, and for identifying small molecules that will disrupt sperm-egg interaction and fertilization.

12 Claims, 31 Drawing Sheets

```
          10                  30                  50
           .                   .                   .

1  GGCCAAGATTTTCAGAATTTCTGCCACTACCAAGGGTATATTGAAGGTTATCCAAAATCT  60
     GlyGlnAspPheGlnAsnPheCysHisTyrGlnGlyTyrIleGluGlyTyrProLysSer 70                  90                  110
           .                   .                   .

61  GTGGTGATGGTTAGCACATGTACTGGACTCAGGGGCGTACTACAGTTTGAAAATGTTAGT 120
     ValValMetValSerThrCysThrGlyLeuArgGlyValLeuGlnPheGluAsnValSer 130                 150                 170
           .                   .                   .

121  TATGGAATAGAACCCCTGGAGTCTTCAGTTGGCTTTGAACATGTAATTTACCAAGTAAAA 180
     TyrGlyIleGluProLeuGluSerSerValGlyPheGluHisValIleTyrGlnValLys 190                 210                 230
           .                   .                   .

181  CATAAGAAAGCAGATGTTTCCTTATATAATGAGAAGGATATTGAATCAAGAGATCTGTCC 240
     HisLysLysAlaAspValSerLeuTyrAsnGluLysAspIleGluSerArgAspLeuSer 250                 270                 290
           .                   .                   .

241  TTTAAAATTACAAAGCGCAGAGCCACAGCAAGATTTTGCAAAGTATATAGAAATGCATGTT 300
     PheLysLeuGlnSerAlaGluProGlnAspPheAlaLysTyrIleGluMetHisVal 310                 330                 350
           .                   .                   .

301  ATAGTTGAAAAACAATTGTATAATCATATGGGGTCTGATACAACTGTTGTCGCTCAAAAA 360
     IleValGluLysGlnLeuTyrAsnHisMetGlySerAspThrThrValValAlaGlnLys
```

361 GTTTTCCAGTTGATTGGATTGACGAATGCTATTTTTGTTTCATTTAATATTACAATTATT 420
    ValPheGlnLeuIleGlyLeuThrAsnAlaIlePheValSerPheAsnIleThrIleIle 430            450            470
      .     .       .      .       .     .

421 CTGTCTTCATTGGAGCTTTGGATAGATGAAAATAAAATTGCAACCACTGGAGAAGCTAAT 480
    LeuSerSerLeuGluLeuTrpIleAspGluAsnLysIleAlaThrThrGlyGluAlaAsn 490            510            530
      .     .       .      .       .     .

481 GAGTTATTACACACATTTTTAAGATGGAAAACATCTTATCTTGTTTTACGTCCTCATGAT 540
    GluLeuLeuHisThrPheLeuArgTrpLysThrSerTyrLeuValLeuArgProHisAsp 550            570            590
      .     .       .      .       .     .

541 GTGGCATTTTTACTTGTTTACAGAGAAAAGTCAAATTATGTTGGTGCAACCTTTCAAGGG 600
    ValAlaPheLeuLeuValTyrArgGluLysSerAsnTyrValGlyAlaThrPheGlnGly 610            630            650
      .     .       .      .       .     .

601 AAGATGTGTGATGCAAACTATGCAGGAGGTGTTGTTCTGCACCCCAGAACCATAAGTCTG 660
    LysMetCysAspAlaAsnTyrAlaGlyGlyValValLeuHisProArgThrIleSerLeu 670            690            710
      .     .       .      .       .     .

661 GAATCACTTGCAGTTATTTTAGCTCAATTATTGAGCCTTAGTATGGGGATCACTTATGAT 720
    GluSerLeuAlaValIleLeuAlaGlnLeuLeuSerLeuSerMetGlyIleThrTyrAsp
```

FIG.1B

```
           730              750              770
721  GACATTAACAAATGCCAGTGCTCAGGAGCTGTCTGCATTATGAATCCAGAAGCAATTCAT  780
     AspIleAsnLysCysGlnCysSerGlyAlaValCysIleMetAsnProGluAlaIleHis 790              810              830
781  TTCAGTGGTGTGAAGATCTTTAGTAACTGCAGCTTCGAAGACTTTGCACATTTTATTTCA  840
     PheSerGlyValLysIlePheSerAsnCysSerPheGluAspPheAlaHisPheIleSer 850              870              890
841  AAGCAGAAGTCCCAGTGTCTTCACAATCAGCCTCGCTTAGATCCTTTTTTCAAACAGCAA  900
     LysGlnLysSerGlnCysLeuHisAsnGlnProArgLeuAspProPhePheLysGlnGln 910              930              950
901  GCAGTGTGTGGTAATGCAAAGCTGGAAGCAGGAGAGGAGTGTGACTGTGGGACTGAACAG  960
     AlaValCysGlyAsnAlaLysLeuGluAlaGlyGluGluCysAspCysGlyThrGluGln 970              990              1010
961  GATTGTGCCCTTATTGGAGAAACATGCTGTGATATTGCCACATGTAGATTTAAAGCCGGT  1020
     AspCysAlaLeuIleGlyGluThrCysCysAspIleAlaThrCysArgPheLysAlaGly 1030             1050             1070
1021 TCAAACTGTGCTGAAGGACCATGCTGCGAAAACTGTCTATTTATGTCAAAAGAAAGAATG  1080
     SerAsnCysAlaGluGlyProCysCysGluAsnCysLeuPheMetSerLysGluArgMet
```

FIG.1C

```
            1090              1110              1130
              .                 .                 .
1081  TGTAGGCCTTCCTTTGAAGAATGCGACCTCCCTGAATATTGCAATGGATCATCTGCATCA 1140
      CysArgProSerPheGluGluCysAspLeuProGluTyrCysAsnGlySerSerAlaSer 1150              1170              1190
              .                 .                 .
1141  TGCCCAGAAAACCACTATGTTCAGACTGGGCATCCGTGTGGACTGAATCAATGGATCTGT 1200
      CysProGluAsnHisTyrValGlnThrGlyHisProCysGlyLeuAsnGlnTrpIleCys 1210              1230              1250
              .                 .                 .
1201  ATAGATGGAGTTTGTATGAGTGGGGATAAACAATGTACAGACACATTTGGCAAAGAAGTA 1260
      IleAspGlyValCysMetSerGlyAspLysGlnCysThrAspThrPheGlyLysGluVal 1270              1290              1310
              .                 .                 .
1261  GAGTTTGGCCCTTCAGAATGTTATTCTCACCTTAATTCAAAGACTGATGTATCTGGAAAC 1320
      GluPheGlyProSerGluCysTyrSerHisLeuAsnSerLysThrAspValSerGlyAsn 1330              1350              1370
              .                 .                 .
1321  TGTGGTATAAGTGATTCAGGATACACACAGTGTGAAGCTGACAATCTGCAGTGCGGAAAA 1380
      CysGlyIleSerAspSerGlyTyrThrGlnCysGluAlaAspAsnLeuGlnCysGlyLys 1390              1410              1430
              .                 .                 .
1381  TTAATATGTAAATATGTAGGTAAATTTTTATTACAAATTCCAAGAGCCACTATTATTTAT 1440
      LeuIleCysLysTyrValGlyLysPheLeuLeuGlnIleProArgAlaThrIleIleTyr
```

1441  GCCAACATAAGTGGACATCTCTGCATTGCTGTGGAATTTGCCAGTGATCATGCAGACAGC  1500
      AlaAsnIleSerGlyHisLeuCysIleAlaValGluPheAlaSerAspHisAlaAspSer 1510              1530              1550
             .                 .                 .

1501  CAAAAGATGTGGATAAAAGATGGAACTTCTTGTGGTTCAAATAAGGTTTGCAGGAATCAA  1560
      GlnLysMetTrpIleLysAspGlyThrSerCysGlySerAsnLysValCysArgAsnGln 1570              1590              1610
             .                 .                 .

1561  AGATGTGTGAGTTCTTCATACTTGGGTTATGATTGTACTACTGACAAATGCAATGATAGA  1620
      ArgCysValSerSerSerTyrLeuGlyTyrAspCysThrThrAspLysCysAsnAspArg 1630              1650              1670
             .                 .                 .

1621  GGTGTATGCAATAACAAAAAGCACTGTCACTGTAGTGCTTCATATTTACCTCCAGATTGC  1680
      GlyValCysAsnAsnLysLysHisCysHisCysSerAlaSerTyrLeuProProAspCys 1690              1710              1730
             .                 .                 .

1681  TCAGTTCAATCAGATCTATGGCCTGGTGGGAGTATTGACAGTGGCAATTTTCCACCTGTA  1740
      SerValGlnSerAspLeuTrpProGlyGlySerIleAspSerGlyAsnPheProProVal 1750              1770              1790
             .                 .                 .

1741  GCTATACCAGCCAGACTCCCTGAAAGGCGCTACATTGAGAACATTTACCATTCCAAACCA  1800
      AlaIleProAlaArgLeuProGluArgArgTyrIleGluAsnIleTyrHisSerLysPro
```

1801  ATGAGATGGCCATTTTTCTTATTCATTCCTTTCTTTATTATTTTCTGTGTACTGATTGCT  1860

MetArgTrpProPhePheLeuPheIleProPhePheIleIlePheCysValLeuIleAla 1870              1890              1910
          .       .         .        .        .

1861  ATAATGGTGAAAGTTAATTTCCAAAGGAAAAAATGGAGAACTGAGGACTATTCAAGCGAT  1920

IleMetValLysValAsnPheGlnArgLysLysTrpArgThrGluAspTyrSerSerAsp 1930              1950              1970
          .       .         .        .        .

1921  GAGCAACCTGAAAGTGAGAGTGAACCTAAAGGGTAGTCTGGACAACAGAGATGCCATGAT  1980

GluGlnProGluSerGluSerGluProLysGly 1990              2010              2030
          .       .         .        .        .

1981  ATCACTTCTTCTAGAGTAATTATCTGTGATGGATGGACACAAAAAAATGGAAAGAAAAGA  2040

2050              2070              2090
          .       .         .        .        .

2041  ATGTACATTACCTGGTTTCCTGGGATTCAAACCTGCATATTGTGATTTTAATTTGACCAG  2100

2110              2130              2150
          .       .         .        .        .

2101  AAAATATGATATATATGTATAATTTCACAGATAATTTACTTATTTAAAAATGCATGATAA  2160
```

FIG.1F

```
              2170              2190              2210
                .         .       .        .        .        .
2161  TGAGTTTTACATTACAAATTTCTGTTTTTTTAAAGTTATCTTACGCTATTTCTGTTGGTT  2220

2230              2250              2270
                .         .       .        .        .        .
2221  AGTAGACACTAATTCTGTCAGTAGGGGCATGGTATAAGGAAATATCATAATGTAATGAGG  2280

2290              2310              2330
                .         .       .        .        .
2281  TGGTACTATGATTAAAAGCCACTGTTACATTTCAAAAAAAAAAAAAAAA  2330
```

FIG.1G

```
      10            30            50
1   GGCACGAGCGATTATGTTGGCGCTACCTATCAAGGGAAGATGTGTGACAAGAACTATGCA  60
    GlyThrSerAspTyrValGlyAlaThrTyrGlnGlyLysMetCysAspLysAsnTyrAla 70            90            110
61  GGAGGAGTTGCTTTGCACCCCAAAGCCGTAACTCTGGAATCACTTGCAATTATTTTAGTT  120
    GlyGlyValAlaLeuHisProLysAlaValThrLeuGluSerLeuAlaIleIleLeuVal 130           150           170
121 CAGCTGCTGAGCCTCAGCATGGGGCTAGCGTATGACGACGTGAACAAGTGCCAGTGTGGC  180
    GlnLeuLeuSerLeuSerMetGlyLeuAlaTyrAspAspValAsnLysCysGlnCysGly 190           210           230
181 GTACCTGTCTGCGTGATGAACCCGGAAGCGCCTCACTCCAGCGGTGTCCGGGCCTTCAGT  240
    ValProValCysValMetAsnProGluAlaProHisSerSerGlyValArgAlaPheSer 250           270           290
241 AACTGCAGCATGGAGGACTTTTCCAAGTTTATCACAAGTCAAAGCTCCCACTGTCTGCAG  300
    AsnCysSerMetGluAspPheSerLysPheIleThrSerGlnSerSerHisCysLeuGln 310           330           350
301 AACCAGCCAACGCTACAGCCATCTTACAAGATGGCGGTCTGTGGGAATGGAGAGGTGGAA  360
    AsnGlnProThrLeuGlnProSerTyrLysMetAlaValCysGlyAsnGlyGluValGlu
```

361  GAAGATGAAATTTGCGACTGTGGAAAGAAGGGCTGTGCAGAAATGCCCCCGCCATGCTGT  420

GluAspGluIleCysAspCysGlyLysLysGlyCysAlaGluMetProProProCysCys 430            450            470
            .      .      .      .      .

421  AACCCCGACACCTGTAAGCTGTCAGATGGCTCCGAGTGCTCCAGCGGGATATGCTGCAAC  480

AsnProAspThrCysLysLeuSerAspGlySerGluCysSerSerGlyIleCysCysAsn 490            510            530
            .      .      .      .      .

481  TCGTGCAAGCTGAAGCGGAAAGGGGAGGTTTGCAGGCTTGCCCAAGATGAGTGTGATGTC  540

SerCysLysLeuLysArgLysGlyGluValCysArgLeuAlaGlnAspGluCysAspVal 550            570            590
            .      .      .      .      .

541  ACAGAGTACTGCAACGGCACATCCGAAGTGTGTGAAGACTTCTTTGTTCAAAACGGTCAC  600

ThrGluTyrCysAsnGlyThrSerGluValCysGluAspPhePheValGlnAsnGlyHis 610            630            650
            .      .      .      .      .

601  CCATGTGACAATCGCAAGTGGATCTGTATTAACGGCACCTGTCAGAGTGGAGAACAGCAG  660

ProCysAspAsnArgLysTrpIleCysIleAsnGlyThrCysGlnSerGlyGluGlnGln 670            690            710
            .      .      .      .      .

661  TGCCAGGATCTATTTGGCATCGATGCAGGCTTTGGTTCAAGTGAATGTTTCTGGGAGCTG  720

CysGlnAspLeuPheGlyIleAspAlaGlyPheGlySerSerGluCysPheTrpGluLeu
```

721  AATTCCAAGAGCGACATATCTGGGAGCTGTGGAATCTCTGCTGGGGGATACAAGGAATGC  780
     AsnSerLysSerAspIleSerGlySerCysGlyIleSerAlaGlyGlyTyrLysGluCys 790              810              830
                     .                .                .

781  CCACCTAATGACCGGATGTGTGGGAAAATAATATGTAAATACCAAAGTGAAAATATACTA  840
     ProProAsnAspArgMetCysGlyLysIleIleCysLysTyrGlnSerGluAsnIleLeu 850              870              890
                     .                .                .

841  AAATTGAGGTCTGCCACTGTTATTTATGCCAATATAAGCGGGCATGTCTGCGTTTCCCTG  900
     LysLeuArgSerAlaThrValIleTyrAlaAsnIleSerGlyHisValCysValSerLeu 910              930              950
                     .                .                .

901  GAATATCCCCAAGGTCATAATGAGAGCCAGAAGATGTGGGTGAGAGATGGAACCGTCTGC  960
     GluTyrProGlnGlyHisAsnGluSerGlnLysMetTrpValArgAspGlyThrValCys 970              990              1010
                     .                .                .

961  GGGTCAAATAAGGTTTGCCAGAATCAAAAATGTGTAGCAGACACTTTCTTGGGCTATGAT  1020
     GlySerAsnLysValCysGlnAsnGlnLysCysValAlaAspThrPheLeuGlyTyrAsp 1030             1050             1070
                     .                .                .

1021 TGCAACCTGGAAAAATGCAACCACCATGGTGTATGTAATAACAAGAAGAACTGCCACTGT  1080
     CysAsnLeuGluLysCysAsnHisHisGlyValCysAsnAsnLysLysAsnCysHisCys
```

FIG.2C

```
           1090              1110              1130
1081  GACCCCACATACTTACCTCCAGATTGTAAAAGAATGAAAGATTCATATCCTGGCGGGAGC  1140
      AspProThrTyrLeuProProAspCysLysArgMetLysAspSerTyrProGlyGlySer 1150              1170              1190
1141  ATTGATAGTGGCAACAAGGAAAGGGCTGAACCCATCCCTGTACGGCCCTACATTGCAAGT  1200
      IleAspSerGlyAsnLysGluArgAlaGluProIleProValArgProTyrIleAlaSer 1210              1230              1250
1201  CGTTACCGCTCCAAGTCTCCACGGTGGCCATTTTTCTTGATCATCCCTTTCTACGTTGTG  1260
      ArgTyrArgSerLysSerProArgTrpProPhePheLeuIleIleProPheTyrValVal 1270              1290              1310
1261  ATCCTTGTCCTGATTGGGATGCTGGTAAAAGTCTATTCCCAAAGGATGAAATGGAGAATG  1320
      IleLeuValLeuIleGlyMetLeuValLysValTyrSerGlnArgMetLysTrpArgMet 1330              1350              1370
1321  GATGACTTCTCAAGCGAAGAGCAATTTGAAAGTGAAAGTGAATCCAAAGACTAGTCTGGA  1380
      AspAspPheSerSerGluGluGlnPheGluSerGluSerGluSerLysAsp 1390              1410              1430
1381  CAGATTCCACAATGTCACAAGTAATTCTCTTCAGTGGACAGAAAAAAAAGTGGAAAAGAA  1440

1450              1470              1490
1441  AAGCCTATGCATTATCTTGCCTGAAAGTCAAGCCTGCATATCGTGGTCTCCATCAGGCCA  1500

1510              1530              1550
1501  GAAATCATATCTCTCCATTACACATGTATGATACATATGTGTGTATATTATTCCATAAAT  1560
```

FIG.2D

```
                      1570                 1590                 1610
1561    GATTTACTTGTAAGAAATGAATGATTATGAATTTCATATTATACTTTGATATTTTACCCT    1620

1630                 1650                 1670
1621    ATTTCTGGTAGTCGGTAGTCATCAATTGTATTTTCTAGTAGGTACATTATAGAAAAGGCT    1680

1690
1681    ATAAGAAAATAAATGTGGTACCA    1703
```

FIG.2E

```
                T
        H       s
        Co              B
        ve      p       sS
        i l     A5      at
        J l     p0      Jy
        l l     o9      l l
                l l
         /       /       /
    GGCCAAGATTTTCAGAATTTCTGCCACTACCAAGGGTATATTGAAGGTTATCCAAAATCT
  1 ─────────┼─────────┼─────────┼─────────┼─────────┼─────────┤ 60
    CCGGTTCTAAAAGTCTTAAAGACGGTGATGGTTCCCATATAACTTCCAATAGGTTTTAGA

B
                 s
                 Ap    N
                 fL    l       BH
         B       HlU   aNPR   siBD       M     R   S
         c       pl1   lsls   pnsd       l     s   f
         c       hl1   lpea   Gfre       y     o   c
         l       l l l   l l l l   l l l l     l   l   l
          /       ///
    GTGGTGATGGTTAGCACATGTACTGGACTCAGGGGCGTACTACAGTTTGAAAATGTTAGT
 61 ─────────┼─────────┼─────────┼─────────┼─────────┼─────────┤ 120
    CACCACTACCAATCGTGTACATGACCTGAGTCCCCGCATGATGTCAAACTTTTACAATCA B
                                             s         T
         E       E                           Ap    N   s
         c       BcMSH              C        fL    l   p
         o       MBsobci     P      v        B lU  oN5
         5       lbaRorn     l      i        p l1  ls0
         7       ysJl lFf    e      J        m l1  lp9
         l       l l l l l l l      l   l    l l l  l l l
                  ////                         /     //
    TATGGAATAGAACCCCTGGAGTCTTCAGTTGGCTTTGAACATGTAATTTACCAAGTAAAA
121 ─────────┼─────────┼─────────┼─────────┼─────────┼─────────┤ 180
    ATACCTTATCTTGGGGACCTCAGAAGTCAACCGAAACTTGTACATTAAATGGTTCATTTT S
                                         H       BB a
                                         iT      gsDu
                                         nf      ltp3
                                         f i     lYnA
                                         l l     l l l l
                                          /       //
    CATAAGAAAGCAGATGTTTCCTTATATAATGAGAAGGATATTGAATCAAGAGATCTGTCC
181 ─────────┼─────────┼─────────┼─────────┼─────────┼─────────┤ 240
    GTATTCTTTCGTCTACAAAGGAATATATTACTCTTCCTATAACTTAGTTCTCTAGACAGG
```

FIG.3A

```
                T
                s
                p                                               N
                M5          C           C               C       l
                srO    H    v           v               v  N   aN
                eo9    h    i           i               i  s   ls
                III    a    J           R               R  i   lp
                 l     I    I           I               I  I   II
                 /                                              /
       TTTAAATTACAAAGCGCAGAGCCACAGCAAGATTTTGCAAAGTATATAGAAATGCATGTT
   241 ─────────┼─────────┼─────────┼─────────┼─────────┼────────── 300
       AAATTTAATGTTTCGCGTCTCGGTGTCGTTCTAAAACGTTTCATATATCTTTACGTACAA

T
                s
                p
                M5          N           B
                u0          d           a
                n9          e           e
                II          I           I
                /
       ATAGTTGAAAAACAATTGTATAATCATATGGGGTCTGATACAACTGTTGTCGCTCAAAAA
   301 ─────────┼─────────┼─────────┼─────────┼─────────┼────────── 360
       TATCAACTTTTTGTTAACATATTAGTATACCCCAGACTATGTTGACAACAGCGAGTTTTT

T
                    B                                   s    M
            B       s                       M      S    p5   Bb
            s       t              B        s      s    09   bo
            r       X              s        e      p    9    sI
            I       I              m        I      I    I    II
                                   I                         /
       GTTTTCCAGTTGATTGGATTGACGAATGCTATTTTTGTTTCATTTAATATTACAATTATT
   361 ─────────┼─────────┼─────────┼─────────┼─────────┼────────── 420
       CAAAAGGTCAACTAACCTAACTGCTTACGATAAAAACAAAGTAAATTATAATGTTAATAA

T
                                s
                                p       C                C
                    C           5       v         B      Av
                    Av          0       i         s      li
                    li          9       R         r      uJ
                    uJ          I       I         I      II
                    II                                   /
       CTGTCTTCATTGGAGCTTTGGATAGATGAAAATAAAATTGCAACCACTGGAGAAGCTAAT
   421 ─────────┼─────────┼─────────┼─────────┼─────────┼────────── 480
       GACAGAAGTAACCTCGAAACCTATCTACTTTTATTTTAACGTTGGTGACCTCTTCGATTA
```

FIG.3B

```
              B          M    B                             M      N
                                                            a    R  l
              p          s    c                             e    c  a
              m          e    c                             l    o  I
              I          I    I                             I    I  I
     GAGTTATTACACACATTTTTAAGATGGAAAACATCTTATCTTGTTTTACGTCCTCATGAT
481  ———————————+———————————+———————————+———————————+———————————+ 540
     CTCAATAATGTGTGTAAAAATTCTACCTTTTGTAGAATAGAACAAAATGCAGGAGTACTA

T
                                    s
                                    p                C            S
         M                          5                v     B      f
         n                          0                i     s      a
         l                          9                R     l      N
         I                          I                I     I      I
     GTGGCATTTTTACTTGTTTACAGAGAAAAGTCAAATTATGTTGGTGCAACCTTTCAAGGG
541  ———————————+———————————+———————————+———————————+———————————+ 600
     CACCGTAAAAATGAACAAATGTCTCTTTTCAGTTTAATACAACCACGTTGGAAAGTTCCC

MC      A  C                   C           D          B
             bv     MpMBv                   v           r          s
             oi     nows i                  i           d          t
             IR     IBogR                   R           l          X
             II     IIIII                   I           I          I
                      //
     AAGATGTGTGATGCAAACTATGCAGGAGGTGTTGTTCTGCACCCCAGAACCATAAGTCTG
601  ———————————+———————————+———————————+———————————+———————————+ 660
     TTCTACACACTACGTTTGATACGTCCTCCACAACAAGACGTGGGGTCTTGGTATTCAGAC T
                              s                       S
         H       C          C p             C         a
         iT      v          Av 5            v D   B   u  D      A
         nf      i          li 0            i d   s   3  p      l
         fi      R          uJ 9            J e   l   A  n      w
         II      I          II I            I I   I   I  I      I
          /                   /
     GAATCACTTGCAGTTATTTTAGCTCAATTATTGAGCCTTAGTATGGGGATCACTTATGAT
661  ———————————+———————————+———————————+———————————+———————————+ 720
     CTTAGTGAACGTCAATAAAATCGAGTTAATAACTCGGAATCATACCCCTAGTGAATACTA
```

FIG.3C

```
                                     B
                                     s
                                     BAp
                                     pI1       A C          C        H              T
                                                                                    s
             M         B             uw2D     A l v         v        i T            p
             s         s             128d     l w i         i        n f            5X
             e         r             016e     u N J         R        f i            0m
             l         l             1111     I I I         I        I I            9n
                                     //       //                     /              I I
                                                                                    /
           GACATTAACAAATGCCAGTGCTCAGGAGCTGTCTGCATTATGAATCCAGAAGCAATTCAT
       721 ─────┼─────┼─────┼─────┼─────┼─────┼ 780
           CTGTAATTGTTTACGGTCACGAGTCCTCGACAGACGTAATACTTAGGTCTTCGTTAAGTA

S        M         F
                     BB       o M      Cn        C                 C      M        B
              M      gsDu     e bB  S  vuPAv     NT       B        B v    b        s       B
              s      ltp3     l oc  f  i4sli     sa       b        b i    o        m       c
              l      lYnA     l lg  c  RHLuJ     pq       v        s R    l        F       g
              l      1111     1 1 1 1  1 1 1 1 1 VI       I        I I    I        I       I
                     //                /         //
           TTCAGTGGTGTGAAGATCTTTAGTAACTGCAGCTTCGAAGACTTTGCACATTTTATTTCA
       781 ─────┼─────┼─────┼─────┼─────┼─────┼ 840
           AAGTCACCACACTTCTAGAAATCATTGACGTCGAAGCTTCTGAAACGTGTAAAATAAAGT S
                     M                     C              Ba                 C
                     BbB                   v    A D       suDM               o
                     bos                   i    l d       t3pn               c
                     slr                   J    w e       YAnl               8
                     1 1 1                 I    I I       1 1 1 1            I
                                                          //
           AAGCAGAAGTCCCAGTGTCTTCACAATCAGCCTCGCTTAGATCCTTTTTTCAAACAGCAA
       841 ─────┼─────┼─────┼─────┼─────┼─────┼ 900
           TTCGTCTTCAGGGTCACAGAAGTGTTAGTCGGAGCGAATCTAGGAAAAAAGTTTGTCGTT T        T
                     t        t
                     h        h
                     1        1                                  M    T
                     1        1 C        C                 BR    o    s
                     1        1 v        Av      M         sl    e    p
                     1        1 i        li      n         ee    l    4
                     l        l R        uJ      l         RA    1    5
                     l        l l        l l     l         l l   l    l
                                         /                 /
           GCAGTGTGTGGTAATGCAAAGCTGGAAGCAGGAGAGGAGTGTGACTGTGGGACTGAACAG
       901 ─────┼─────┼─────┼─────┼─────┼─────┼ 960
           CGTCACACACCATTACGTTTCGACCTTCGTCCTCTCCTCACACTGACACCCTGACTTGTC
```

FIG.3D

```
              B                          B
              s                          s
              p             N            Ap  N
          B   1             I            fL  I              BC
          s   2             oN           IU  oN      MD     svM
          m   8             Is           II  Is      sr     ris
          F   6             Ip           II  Ip      eo     FJp
          I   I             II           II  II      II     III
                            /            /   /              ///
     GATTGTGCCCTTATTGGAGAAACATGCTGTGATATTGCCACATGTAGATTTAAAGCCCGGT
961  ────────┼─────────┼─────────┼─────────┼─────────┼─────────┼──── 1020
     CTAACACGGGAATAACCTCTTTGTACGACACTATAACGGTGTACATCTAAATTTCGGCCA S         NF         E
                   Aa         In         c
              B    vu         ou         o
              b    a9         I4         5
              v    I6         IH         7
              I    II         II         I
                   /
     TCAAACTGTGCTGAAGGACCATGCTGCGAAAACTGTCTATTTATGTCAAAAGAAAGAATG
1021 ────────┼─────────┼─────────┼─────────┼─────────┼─────────┼──── 1080
     AGTTTGACACGACTTCCTGGTACGACGCTTTTGACAGATAAATACAGTTTTCTTTCTTAC H                                   S
          C   a                              C    a  B           C
          vHeS              M              MS v    u sD          Av
          ialt          B   b              ns i    3 rp          li
          Jelu          s   o              Ip R    A Dn          wR
          IIII          m   I              II I    I II          II
          ///                               /        /
     TGTAGGCCTTCCTTTGAAGAATGCGACCTCCCTGAATATTGCAATGGATCATCTGCATCA
1081 ────────┼─────────┼─────────┼─────────┼─────────┼─────────┼──── 1140
     ACATCCGGAAGGAAACTTCTTACGCTGGAGGGACTTATAACGTTACCTAGTAGACGTAGT N                                                     S
          I  S                              S       H           Ba
          a  f             F            B   M       iT          suD
          I  a             o            s   s       nf          t3p
          I  N             k            r   I       fi          YAn
          I  I             I            I   I       II          III
                                                     /           /
     TGCCCAGAAAACCACTATGTTCAGACTGGGCATCCCTGTGGACTGAATCAATGGATCTGT
1141 ────────┼─────────┼─────────┼─────────┼─────────┼─────────┼──── 1200
     ACGGGTCTTTTGGTGATACAAGTCTGACCCGTAGGCACACCTGACTTAGTTACCTAGACA
```

FIG.3E

```
                                    B
                                    s
                                    p
                                    1
         A      B                   4   R                      E
         l      c                   0   s                      c
         w      c                   7   a                      o
         I      I                   I   I                      5
                                                               7
                                                               I
         ATAGATGGAGTTTGTATGAGTGGGGATAAACAATGTACAGACACATTTGGCAAAGAAGTA
1201 ────┼─────────┼─────────┼─────────┼─────────┼─────────┼──── 1260
         TATCTACCTCAAACATACTCACCCCTATTTGTTACATGTCTGTGTAAACCGTTTCTTCAT

T
         S  H                       s
         a C a                      p
         u v e          H           M 5
         9 i l          p           s 0              B
         6 J l          h           e 9              a
         I I I          I           I I              e
                                                     I
         /
         GAGTTTGGCCCTTCAGAATGTTATTCTCACCTTAATTCAAAGACTGATGTATCTGGAAAC
1261 ────┼─────────┼─────────┼─────────┼─────────┼─────────┼──── 1320
         CTCAAACCGGGAAGTCTTACAATAAGAGTGGAATTAAGTTTCTGACTACATAGACCTTTG

T
                                                                s
                            D  D                                p
                H           r  r        C           C           5
                i T         a  a        A v    P    S v  P  A   0
                n f         l  l        l i    s    f i  s  c   9
                f i         I  I        u J    R t  c R  t  i   I
                I I                     I I         I I  I  I
                                        /
         TGTGGTATAAGTGATTCAGGATACACACAGTGTGAAGCTGACAATCTGCAGTGCGGAAAA
1321 ────┼─────────┼─────────┼─────────┼─────────┼─────────┼──── 1380
         ACACCATATTCACTAAGTCCTATGTGTGTCACACTTCGACTGTTAGACGTCACGCCTTTT

T            T
                             s            s
                             p            p             C
         M V                 A 5          A 5           v
         s s                 p 0          p 0           i
         e p                 o 9          o 9           J
         I I                 I I          I I           I
         /                   /            /
         TTAATATGTAAATATGTAGGTAAATTTTTATTACAAATTCCAAGAGCCACTATTATTTAT
1381 ────┼─────────┼─────────┼─────────┼─────────┼─────────┼──── 1440
         AATTATACATTTATACATCCATTTAAAAATAATGTTTAAGGTTCTCGGTGATAATAAATA
```

FIG.3F

```
                            T
                            s                S        N
              BC            p                a        Cl       C
              sv    M       A5       B       BuD      va       v
              ri    s       p0       s       c3p      il       i
              DR    I       o9       r       lAn      RI       J
              II    I       II       I       III      II       I
                   /         /               /        /
         GCCAACATAAGTGGACATCTCTGCATTGCTGTGGAATTTGCCAGTGATCATGCAGACAGC
    1441 ─────┼─────────┼─────────┼─────────┼─────────┼─────────┼ 1500
         CGGTTGTATTCACCTGTAGAGACGTAACGACACCTTAAACGGTCACTAGTACGTCTGTCG

D                  C       H
                 B            r                  v       iT
                 c            d                  i       nf
                 c            l                  R       fi
                 I            I                  I       II
                                                         /
         CAAAAGATGTGGATAAAAGATGGAACTTCTTGTGGTTCAAATAAGGTTTGCAGGAATCAA
    1501 ─────┼─────────┼─────────┼─────────┼─────────┼─────────┼ 1560
         GTTTTCTACACCTATTTTCTACCTTGAAGAACACCAAGTTTATTCCAAACGTCCTTAGTT

M                                       C      B
             b                       R               vM     s
             o                       s               in     r
             I                       a               RI     D
             I                       I               II     I
         AGATGTGTGAGTTCTTCATACTTGGGTTATGATTGTACTACTGACAAATGCAATGATAGA
    1561 ─────┼─────────┼─────────┼─────────┼─────────┼─────────┼ 1620
         TCTACACACTCAAGAAGTATGAACCCAATACTAACATGATGACTGTTTACGTTACTATCT

M  T
              C        o  s
              v        e  p    S  M   B                          MD
              i        1  4    f  s   p                          nd
              R        1  5    c  l   m                          le
              I        I  I    I  I   I                          II
         GGTGTATGCAATAACAAAAAGCACTGTCACTGTAGTGCTTCATATTTACCTCCAGATTGC
    1621 ─────┼─────────┼─────────┼─────────┼─────────┼─────────┼ 1680
         CCACATACGTTATTGTTTTTCGTGACAGTGACATCACGAAGTATAAATGGAGGTCTAACG
```

FIG.3G

```
                        T
        S       E H     s
       BB o    Cc oS    p
       gsDu    voHec    5              S
       Itp3    iRalr    0              f
       IYnA    JIeIF    9              c
       IIII    IIIII    I              I
         //    ////
      TCAGTTCAATCAGATCTATGGCCTGGTGGGAGTATTGACAGTGGCAATTTTCCACCTGTA
1681  ─────────+─────────+─────────+─────────+─────────+─────────+ 1740
      AGTCAAGTTAGTCTAGATACCGGACCACCCTCATAACTGTCACCGTTAAAAGGTGGACAT C       C   H                   H
       Av     MP v i          M        Ha
       Ii     wl i n          I        he
       uJ     oe J f          y        al
       II     II I I          I        II
        /
      GCTATACCAGCCAGACTCCCTGAAAGGCGCTACATTGAGAACATTTACCATTCCAAACCA
1741  ─────────+─────────+─────────+─────────+─────────+─────────+ 1800
      CGATATGGTCGGTCTGAGGGACTTTCCGCGATGTAACTCTTGTAAATGGTAAGGTTTGGT H
       B    C a
       s   BEvHeM                              R
       t   caials                              s
       X   ceJeIc                              a
       I   IIIIIII                             I
        /  ////
      ATGAGATGGCCATTTTTCTTATTCATTCCTTTCTTTATTATTTTCTGTGTACTGATTGCT
1801  ─────────+─────────+─────────+─────────+─────────+─────────+ 1860
      TACTCTACCGGTAAAAAGAATAAGTAAGGAAAGAAATAATAAAAGACACATGACTAACGA T
              s
              p
             M5   H           M    D
             s0   p           n    d
             e9   h           I    e
             II   I           I    I
      ATAATGGTGAAAGTTAATTTCCAAACGAAAAAATGGAGAACTGAGGACTATTCAAGCGAT
1861  ─────────+─────────+─────────+─────────+─────────+─────────+ 1920
      TATTACCACTTTCAATTAAAGGTTTGCTTTTTTACCTCTTGACTCCTGATAAGTTCGCTA
```

```
                  T
                  s
                  p
                  A 5            M D
                  p 0            s r
                  o 9            e a
                  I I            I I
                     /
      TGAGTTTTACATTACAAATTTCTGTTTTTTTAAAGTTATCTTACGCTATTTCTGTTGGTT
2161  ------------+---------+---------+---------+---------+---------+  2220
      ACTCAAAATGTAATGTTTAAAGACAAAAAAAATTTCAATAGAATGCGATAAAGACAACCAA

T
                   s
                   p            N
             A     5            I              M
             c     0            a              n
             c     9            l              l
             I     I            I              I
      AGTAGACACTAATTCTGTCAGTAGGGGCATGGTATAAGGAAATATCATAATGTAATGAGG
2221  ------------+---------+---------+---------+---------+---------+  2280
      TCATCTGTGATTAAGACAGTCATCCCCGTACCATATTCCTTTATAGTATTACATTACTCC

M
                         C    a
             R      M    v    e
             s      s    i    I
             a      e    J    I
             I      I    I    I
      TGGTACTATGATTAAAAGCCACTGTTACATTTCAAAAAAAAAAAAAAAAAA
2281  ------------+---------+---------+---------+---------+  2330
      ACCATGATACTAATTTTCGGTGACAATGTAAAGTTTTTTTTTTTTTTTTTT
```

Enzymes that do cut:

| | | | | | | | |
|---|---|---|---|---|---|---|---|
| AccI | AciI | AflIII | AluI | AlwI | Alw21I | AlwNI | ApaBI |
| ApoI | AvaII | BaeI | BbsI | BbvI | BccI | BcgI | BclI |
| BfaI | BglI | BpmI | Bpu10I | BsaJI | BseRI | BsgI | BsII |
| BsmI | BsmFI | Bsp1286I | Bsp1407I | BspGI | BspLU11I | BspMI | BsrI |
| BsrDI | BsrFI | BstXI | BstYI | Cac8I | CviJI | CviRI | DdeI |
| DpnI | DraI | DraIII | DrdII | EaeI | Eco57I | EcoRII | EcoRV |
| Fnu4HI | FokI | HaeI | HaeII | HaeIII | HhaI | HinfI | HphI |
| MaeII | MaeIII | MboII | MlyI | MnlI | MscI | MseI | MslI |
| MspI | MunI | MwoI | NdeI | NlaIII | NsiI | NspI | NspV |
| PleI | PstI | RcaI | RleAI | RsaI | Sau96I | Sau3AI | ScrFI |
| SexAI | SfaNI | SfcI | SspI | StuI | StyI | TaqI | TfiI |
| Tsp45I | Tsp509I | Tth111I | VspI | XbaI | XmnI | | |

FIG.3J

Enzymes that do not cut:

| | | | | | | | |
|---|---|---|---|---|---|---|---|
| AatII | AflII | AgeI | Alw44I | ApaI | AscI | AvaI | AvrII |
| BamHI | BanI | BanII | Bce83I | BcefI | BglI | Bpu1102I | BsaI |
| BsaAI | BsaBI | BsaHI | BsaWI | BscGI | BsiI | BsiEI | BsiWI |
| BsmAI | BspEI | BsrBI | BssHII | Bst1107I | BstEII | Bsu36I | ClaI |
| DrdI | DsaI | EagI | Eam1105I | EarI | EciI | Eco47III | Eco105I |
| EcoNI | EcoO109I | EcoRI | Esp3I | FauI | FseI | FspI | GdiII |
| HgaI | HgiEII | HincII | HindIII | HpaI | KpnI | MluI | MmeI |
| NaeI | NarI | NciI | NcoI | NheI | NlaIV | NotI | NruI |
| NspBII | PacI | Pfl1108I | PflMI | PmeI | PmlI | PshAI | Psp5II |
| Psp1406I | PvuI | PvuII | RsrII | SacI | SacII | SalI | SapI |
| ScaI | SfiI | SgrAI | SmaI | SpeI | SphI | SrfI | Sse8387I |
| SwaI | TaqII | TaqII | ThaI | Tth111I | XcmI | XhoI | |

FIG.3K

```
                                      M T
                                      a s
                          H           e s    M
              B           H a     B   p b    M           C
              s           h e     s   l 4    o     M     v
              i           e       i   1 5    o     n     i
              I           o l     I   I I    I     I     R
                          I I                       I    I
              GGCACGAGCGATTATGTTGGCGCTACCTATCAAGGGAAGATGTGTGACAAGAACTATGCA
          1 ─────────┼─────────┼─────────┼─────────┼─────────┼─────── 60
              CCGTGCTCGCTAATACAACCGCGATGGATAGTTCCCTTCTACACACTGTTCTTGATACGT
```

```
                                          T
                               M          s
              B   B   C    C   a      H   C p
              s   c   v    v   e      i T v 5    B
              e   e   i    i   I      n f i 0    b
              R   f   R    J   I      f i R 9    v
              I   I   I    I I        I I  I I   I
              GGAGGAGTTGCTTTGCACCCCAAAGCCGTAACTCTGGAATCACTTGCAATTATTTTAGTT
         61 ─────────┼─────────┼─────────┼─────────┼─────────┼─────── 120
              CCTCCTCAACGAAACGTGGGGTTTCGGCATTGAGACCTTAGTGAACGTTAATAAAATCAA
```

```
              B
              p
         F u N    B         N
         CnA1 sPC p         I  C C         M
         Avu11Dpvv uD    B  aM vBaN        a             B    BM
         1i4w0dBui 1d    s  1n ifch        e             s    gw
         uJHN2e11J 0e    I  II JaBe        I             r    1o
         IIIIIIIII II    I  II IIII        I             I    II
              /  ///    /         /                             /
              CAGCTGCTGAGCCTCAGCATGGGGCTAGCGTATGACGACGTGAACAAGTGCCAGTGTGGC
        121 ─────────┼─────────┼─────────┼─────────┼─────────┼─────── 180
              GTCGACGACTCGGAGTCGTACCCCGATCGCATACTGCTGCACTTGTTCACGGTCACACCG
```

```
                                    E  N      S   H       M
                              S     c  s      aSCa        a
              R             BMNc    Ha o AMp  MNucve      e
              s             pscr    he 5 cnB  sc9ril      I
              a             mpiF    a l 7 i I I pi6FJI    I
              I             IIII    II I III  IIIIII      I
                              //    //         //
              GTACCTGTCTGCGTGATGAACCCGGAAGCGCCTCACTCCAGCGGTGTCCGGGCCTTCAGT
        181 ─────────┼─────────┼─────────┼─────────┼─────────┼─────── 240
              CATGGACAGACGCACTACTTGGGCCTTCGCGGAGTGAGGTCGCCACAGGCCCGGAAGTCA
```

FIG.4A

```
          F      N
   A  Cn   I                           C              C
   lS vuMP a   B                       Av             S v P
   wf i4ns l   b                       li             f i s
   Nc RHlt l   v                       uJ             c R t
   ll llll l   l                       ll             l l l
        //
     AACTGCAGCATGGAGGACTTTTCCAAGTTTATCACAAGTCAAAGCTCCCACTGTCTGCAG
241  ─────┼─────────┼─────────┼─────────┼─────────┼─────────┼─────  300
     TTGACGTCGTACCTCCTGAAAAGGTTCAAATAGTGTTCAGTTTCGAGGGTGACAGACGTC D  C              C           R
     rM v       S   v B            l B A        M
     dw i       f   i c            e c c        n
     lo J       c   J c            A c i        l
     ll l       l   l l            l l l        l
     AACCAGCCAACGCTACAGCCATCTTACAAGATGGCGGTCTGTGGGAATGGAGAGGTGGAA
301  ─────┼─────────┼─────────┼─────────┼─────────┼─────────┼─────  360
     TTGGTCGGTTGCGATGTCGGTAGAATGTTCTACCGCCAGACACCCTTACCTCTCCACCTT T
        s
        pM  M             C   C                        MN
        A5b b             v   v             A          al
        p0o o             i   i             c          BFeo
        o91 l             J   R             i          soll
        lll l             l   l             l          llll
         /                                              //
     GAAGATGAAATTTGCGACTGTGGAAAGAAGGGCTGTGCAGAAATGCCCCCGCCATGCTGT
361  ─────┼─────────┼─────────┼─────────┼─────────┼─────────┼─────  420
     CTTCTACTTTAAACGCTGACACCTTTCTTCCCGACACGTCTTTACGGGGGCGGTACGACA B
                                       s
                                       A p  N              F
                   C       CN          l l  s              n C
                   Av    B B vl   M F  wB2 Ap   M    u v   B
                   li    p c io   w a  2b8 cB   w    4 i   s
                   uJ    m c Jl   o u  1v6 il   o    H R   i
                   ll    l l lV   l l  lll ll   l    l l   l
                    /                  //   /
     AACCCCGACACCTGTAAGCTGTCAGATGGCTCCGAGTGCTCCAGCGGGATATGCTGCAAC
421  ─────┼─────────┼─────────┼─────────┼─────────┼─────────┼─────  480
     TTGGGGCTGTGGACATTCGACAGTCTACCGAGGCTCACGAGGTCGCCCTATACGACGTTG
```

FIG.4B

```
                  E                          M T
      A C C  C    cC C C C                   o s
      Mp v a Av   ov a v a                   e p
      wa i c li   5i c i c        A M        l 4
      oB R 8 uJ   7R 8 J 8        c n        l 5
      II I I II   II I I I        i l        I I
                /
      TCGTGCAAGCTGAAGCGGAAAGGGGAGGTTTGCAGGCTTGCCCAAGATGAGTGTGATGTC
481 ─────┼─────────┼─────────┼─────────┼─────────┼─────────┼───── 540
      AGCACGTTCGACTTCGCCTTTCCCCTCCAAACGTCCGAACGGGTTCTACTCACACTACAG
```

```
                                                              BMT
             C                      B              M          sas
      FRS    v                      c        B     b     H    tep
      osc    i                      e        b     o     p    EI4
      koa    R                      f        s     l     h    II5
      III    I                      I        I     I     I    III
         /                                                       /
      ACAGAGTACTGCAACGGCACATCCGAAGTGTGTGAAGACTTCTTTGTTCAAAACGGTCAC
541 ─────┼─────────┼─────────┼─────────┼─────────┼─────────┼───── 600
      TGTCTCATGACGTTGCCGTGTAGGCTTCACACACTTCTGAAGAAACAAGTTTTGCCAGTG
```

```
      MNT            S
      als     T      Ba                N           B
      M eap   a      suD     AM    B   l           c
      s II4   q      t3p     Is    a   a           e
      l II5   l      YAn     we    n   l           f
      I III   I      III     II    I   V           I
                   /
      CCATGTGACAATCGCAAGTGGATCTGTATTAACGGCACCTGTCAGAGTGGAGAACAGCAG
601 ─────┼─────────┼─────────┼─────────┼─────────┼─────────┼───── 660
      GGTACACTGTTAGCGTTCACCTAGACATAATTGCCGTGGACAGTCTCACCTCTTGTCGTC
```

```
      E        S
      c S Ba       S            CSC C     D                   C
      o c suD X f  A     CT     vfa v     r                   Av A
      R r t3p c a  l     la     iac i     d                   li p
      I F YAn m N  w     aq     RN8 J     I                   uJ o
      I I III I I  I     II     III I     I                   II I
             /              /                                   /
      TGCCAGGATCTATTTGGCATCGATGCAGGCTTTGGTTCAAGTGAATGTTTCTGGGAGCTG
661 ─────┼─────────┼─────────┼─────────┼─────────┼─────────┼───── 720
      ACGGTCCTAGATAAACCGTAGCTACGTCCGAAACCAAGTTCACTTACAAAGACCCTCGAC
```

FIG.4C

```
            T
            s
  Ep                           C       H
  c5                           Av      iT
  o0                           li      nf
  R9                           uJ      fi
  II                           II      II
  //                            /       /
    AATTCCAAGAGCGACATATCTGGGAGCTGTGGAATCTCTGCTGGGGGATACAAGGAATGC
721 ─────┼─────┼─────┼─────┼─────┼─────┼ 780
    TTAAGGTTCTCGCTGTATAGACCCTCGACACCTTAGAGACGACCCCCTATGTTCCTTACG

R  B
      B     l  sM          F                        M
      s     e  os          o                        n
      m     A  Wp          k                        I
      I     I  II          I                        I
    CCACCTAATGACCGGATGTGTGGGAAAATAATATGTAAATACCAAAGTGAAAATATACTA
781 ─────┼─────┼─────┼─────┼─────┼─────┼ 840
    GGTGGATTACTGGCCTACACACCCTTTTATTATACATTTATGGTTTCACTTTTATATGAT

T
   s                                   N         E
   p                          C        I         BcS
   5               F          A  a     aN        soc
   0               a          c  c     Is        aRr
   9               u          i  8     Ip        JIF
   I               I          I  II    II        III
                                                  /
    AAATTGAGGTCTGCCACTGTTATTTATGCCAATATAAGCGGGCATGTCTGCGTTTCCCTG
841 ─────┼─────┼─────┼─────┼─────┼─────┼ 900
    TTTAACTCCAGACGGTGACAATAAATACGGTTATATTCGCCCGTACAGACGCAAAGGGAC B         RCT        M         N
          sS        Iva        b     B   HFl       AB
          at        eiq        o     c   paa       cs
          Jy        AJI        I     c   hul       il
          II        III        I     I   IIV       II
                                              /     /
    GAATATCCCCAAGGTCATAATGAGAGCCAGAAGATGTGGGTGAGAGATGGAACCGTCTGC
901 ─────┼─────┼─────┼─────┼─────┼─────┼ 960
    CTTATAGGGGTTCCAGTATTACTCTCGGTCTTCTACACCCACTCTCTACCTTGGCAGACG
```

FIG.4D

```
                            H                                    C
                            i T                                  v       M
                            n f                                  i       w
                            f i                                  J       o
                            I I                                  I       I
                                /
       GGGTCAAATAAGGTTTGCCAGAATCAAAAATGTGTAGCAGACACTTTCTTGGGCTATGAT
  961 ─────┼─────┼─────┼─────┼─────┼─────┼───── 1020
       CCCAGTTTATTCCAAACGGTCTTAGTTTTTACACATCGTCTGTGAAAGAACCCGATACTA

E                        N                M   T
         C    c  S            C     B     I               Mo   s
         v    o  c             v     s D M N a S          b e  p
         i    R  r             i     o s s c I t          o l  4
         R    I  F             R     J a I o l y          I I  5
         I    I  I             I     I I I I I I          I I  I
                                        / / /
       TGCAACCTGGAAAAATGCAACCACCATGGTGTATGTAATAACAAGAAGAACTGCCACTGT
 1021 ─────┼─────┼─────┼─────┼─────┼─────┼───── 1080
       ACGTTGGACCTTTTTACGTTGGTGGTACCACATACATTATTGTTCTTCTTGACGGTGACA

E
                           R                H   B    c   S
         B                 I       M       i T  s F  o   c   A
         p                 e       n       n f  o a  R   r   c
         m                 A       I       f i  B u  l   F   i
         I                 I       I       I I  I I  I   I   I
                                               /
       GACCCCACATACTTACCTCCAGATTGTAAAAGAATGAAAGATTCATATCCTGGCGGGAGC
 1081 ─────┼─────┼─────┼─────┼─────┼─────┼───── 1140
       CTGGGGTGTATGAATGGAGGTCTAACATTTTCTTACTTTCTAAGTATAGGACCGCCCTCG

S H
                        C                a C a  B         C   B
               F        v        B       R  u v e  s      v   c
               o        i        c       s   9 i I  r     i   e
               k        J        c       a   6 J I  D     R   f
               I        I        I       I   I I I  I     I   I
                                              /
       ATTGATAGTGGCAACAAGGAAAGGGCTGAACCCATCCCTGTACGGCCCTACATTGCAAGT
 1141 ─────┼─────┼─────┼─────┼─────┼─────┼───── 1200
       TAACTATCACCGTTGTTCCTTTCCCGACTTGGGTAGGGACATGCCGGGATGTAACGTTCA
```

FIG.4E

```
                                                                    S
                M                                                   a
                a              H              S                     u
                e       B      BB     C   a   a              M      3
                I       A  s   ssD   E vFHeM  BuD           aA      A
                I       c  r   ams   a iools  c3p           eI      I
                I       i  B   JAa   e Jkelc  IAn           Iw
                I       I  I   III   I IIIII  III           II      I
                                /         ///        /
       CGTTACCGCTCCAAGTCTCCACGGTGGCCATTTTTCTTGATCATCCCTTTCTACGTTGTG
1201 ──────────┼──────────┼──────────┼──────────┼──────────┼────── 1260
       GCAATGGCGAGGTTCAGAGGTGCCACCGGTAAAAAGAACTAGTAGGGAAAGATGCAACAC B
                    S                                       c
             D      f                      F                e      F
             p      a                      o                8      o
             n      N                      k                3      k
             I      I                      I                I      I
       ATCCTTGTCCTGATTGGGATGCTGGTAAAAGTCTATTCCCAAAGGATGAAATGGAGAATG
1261 ──────────┼──────────┼──────────┼──────────┼──────────┼────── 1320
       TAGGAACAGGACTAACCCTACGACCATTTTCAGATAAGGGTTTCCTACTTTACCTCTTAC T
                           s
                           p         M             H
                 ESF       5         b             iT       SB     B
                 aaa       0         o             nf       pf     s
                 rpk       9         I             fi       ea     p
                 III       I         I             II       II     G
                  /                                 /              I
       GATGACTTCTCAAGCGAAGAGCAATTTGAAAGTGAAAGTGAATCCAAAGACTAGTCTGGA
1321 ──────────┼──────────┼──────────┼──────────┼──────────┼────── 1380
       CTACTGAAGAGTTCGCTTCTCGTTAAACTTTCACTTTCACTTAGGTTTCTGATCAGACCT T
                     MET        s
              H      acs    M   p
              iT     eop    b   5           E
              nf     154    o   0           a
              fi     175    I   9           r
              II     III    I   I           I
               /
       CAGATTCCACAATGTCACAAGTAATTCTCTTCAGTGGACAGAAAAAAAAGTGGAAAAGAA
1381 ──────────┼──────────┼──────────┼──────────┼──────────┼────── 1440
       GTCTAAGGTGTTACAGTGTTCATTAAGAGAAGTCACCTGTCTTTTTTTTCACCTTTTCTT
```

```
                                                        H
   C     C                    C C C            B    C a
   v     v  N                 v a v           BBs   vHe
   i     i  s                 i c i           csm   ial
   J     R  i                 J 8 R           coA   Jel
   I     I  I                 I I I           III   III
                                               //    //
     AAGCCTATGCATTATCTTGCCTGAAAGTCAAGCCTGCATATCGTGGTCTCCATCAGGCCA
1441 ————————+————————+————————+————————+————————+————————+ 1500
     TTCGGATACGTAATAGAACGGACTTTCAGTTCGGACGTATAGCACCAGAGGTAGTCCGGT B
              s
              Ap   N
              fL   I
              IU  MoN       BN  M
              II  sIs       od  s
              II  IIp       ee  I
              II  III       II  I
                /    /       /
     GAAATCATATCTCTCCATTACACATGTATGATACATATGTGTGTATATTATTCCATAAAT
1501 ————————+————————+————————+————————+————————+————————+ 1560
     CTTTAGTATAGAGAGGTAATGTGTACATACTATGTATACACACATATAATAAGGTATTTA T
                       s
                       p
                       A5
                       p0
                       o9
                       II
                        /
     GATTTACTTGTAAGAAATGAATGATTATGAATTTCATATTATACTTTGATATTTTACCCT
1561 ————————+————————+————————+————————+————————+————————+ 1620
     CTAAATGAACATTCTTTACTTACTAATACTTAAAGTATAATATGAAACTATAAAATGGGA T
                      s
                      p                              C
              B       M5        B       R            v
              s       u0        f       s            i
              I       n9        o       o            J
              I       II        I       I            I
                       /
     ATTTCTGGTAGTCGGTAGTCATCAATTGTATTTTCTAGTAGGTACATTATAGAAAAGGCT
1621 ————————+————————+————————+————————+————————+————————+ 1680
     TAAAGACCATCAGCCATCAGTAGTTAACATAAAAGATCATCCATGTAATATCTTTTCCGA
```

FIG.4G

```
              N
        B    IRK
        a    asp
        n    Ian
        I    VII
              /
        ATAAGAAAATAAATGTGGTACCA
1681 ————————+————————+—— 1703
        TATTCTTTTATTTACACCATGGT
```

Enzymes that do cut:

| | | | | | | | |
|---|---|---|---|---|---|---|---|
| AciI | AflIII | AluI | AlwI | Alw21I | AlwNI | ApaBI | ApoI |
| BaeI | BanI | BbsI | BbvI | BccI | Bce83I | BcefI | BclI |
| BfaI | BglI | BpmI | Bpu10I | Bpu1102I | BsaI | BsaBI | BsaJI |
| BsaWI | BseRI | BsgI | BsiI | BslI | BsmI | BsmAI | Bsp1286I |
| BspGI | BspLU11I | BsrI | BsrBI | BsrDI | BstEII | BstYI | Cac8I |
| ClaI | CviJI | CviRI | DdeI | DpnI | DrdII | DsaI | EaeI |
| EarI | Eco57I | EcoRI | EcoRII | FauI | Fnu4HI | FokI | HaeI |
| HaeII | HaeIII | HhaI | HinfI | HphI | KpnI | MaeII | MaeIII |
| MboII | MnlI | MscI | MseI | MslI | MspI | MunI | MwoI |
| NciI | NcoI | NdeI | NheI | NlaIII | NlaIV | NsiI | NspI |
| NspBII | PstI | PvuII | RleAI | RsaI | SapI | Sau96I | Sau3AI |
| ScaI | ScrFI | SfaNI | SfcI | SpeI | StyI | TaqI | TaqII |
| TfiI | Tsp45I | Tsp509I | XcmI | | | | |

Enzymes that do not cut:

| | | | | | | | |
|---|---|---|---|---|---|---|---|
| AatII | AccI | AflII | AgeI | Alw44I | ApaI | AscI | AvaI |
| AvaII | AvrII | BamHI | BanII | BcgI | BcgI | BglII | BsaAI |
| BsaHI | BscGI | BsiEI | BsiWI | BsmFI | Bsp1407I | BspEI | BspMI |
| BsrFI | BssHII | Bst1107I | BstXI | Bsu36I | DraI | DraIII | DrdI |
| EagI | Eam1105I | EciI | Eco47III | Eco105I | EcoNI | EcoO109I | EcoRV |
| Esp3I | FseI | FspI | GdiII | HgaI | HgiEII | HincII | HindIII |
| HpaI | MluI | MlyI | MmeI | NaeI | NarI | NotI | NruI |
| NspV | PacI | Pf11108I | PflMI | PleI | PmeI | PmlI | PshAI |
| Psp5II | Psp1406I | PvuI | RcaI | RsrII | SacI | SacII | SalI |
| SexAI | SfiI | SgrAI | SmaI | SphI | SrfI | Sse8387I | SspI |
| StuI | SwaI | ThaI | Tth111I | Tth111II | VspI | XbaI | XhoI |
| XmnI | | | | | | | |

FIG.4H

CONTRACEPTIVE VACCINE

This application is a national stage entry of PCT/US95/07295 filed Jun. 6, 1995, which is a continuation-in-part of U.S. application Ser. No. 08/264,101 filed Jun. 20, 1994, now U.S. Pat. No. 5,693,496.

FIELD OF THE INVENTION

The present invention provides sperm surface proteins and DNA sequences encoding the proteins which are useful in the prevention of fertilization. More particularly, the cloning and characterization of the mouse and human PH30 beta chain genes, as well as their use as contraceptive vaccines, are described.

BACKGROUND OF THE INVENTION

Four methods of family planning are currently available in the U.S., sterilization, abstinence, abortion and contraception. Of these four birth control methods, contraception is the most widely utilized. Despite the substantial U.S. and global demand for contraception, the presently available methodologies fall short of market needs. Oral contraceptives and barrier methods dominate today's contraceptive market but have significant shortcomings. Oral contraceptives, though efficacious, are documented to be associated with significant side effects including increased risks of cardiovascular disease and breast cancer and are not recommended for women over the age of 35. Barrier methods, while safe, have failure rates approaching 20%. There is a clear need for increased availability of and improvements in contraceptives that offer superior safety, efficacy, convenience, acceptability and are affordable to women and men worldwide. Identification of novel approaches for controlling fertility is therefore necessary.

Immunization of male and female animals with extracts of whole sperm is known to cause infertility. [Tung, K., et al., J. Reproductive Immunol., 1; 145–158 (1979); Menge, A., et al., Biol. of Reproduction, 20, 931–937 (1979)]. Moreover, men and women who spontaneously produce antisperm antibodies are infertile, but otherwise healthy. [Bronson, R., et al., Fert. and Sterile, 42, 171–183 (1984)]. Although the critical sperm antigens are unknown, these observations have led to the proposal that sperm proteins might be useful in the development of a contraceptives vaccine.

In mammalian species, sperm proteins are believed to have a role in sperm adhesion to the zona pellucida of the egg. The PH30 protein is known to be involved in sperm egg binding and antibodies that bind to PH30 inhibit this interaction. PH30 is an integral membrane protein present on posterior head of sperm which mediates sperm-oocyte fusion. The PH30 protein consists of two immunologically distinct alpha and beta subunits. Both subunits are made as larger precursors and then finally processed in epididymis where sperm become fertilization competent. [Primakoff, P., et al., J. Cell Biology, 104, 141–149 (1987); Blobel, C. P., et al., J. Cell Biology, 111, 69–78 (1990)]. Monoclonal antibodies that recognize PH30 inhibit sperm-oocyte fusion in vitro, indicating its importance in fertilization [Primakoff, P., et al., J. Cell Biology, 104, 141–149 (1987)].

Guinea pig PH30 alpha and beta chains have been cloned by Blobel et al. Mature PH30 alpha chain consists of 289 amino acids and encodes a transmembrane domain as well as an integral fusion peptide (82–102) that is similar to a potential fusion peptide of E2 glycoprotein of rubella virus. Guinea Pig PH30 beta chain has an open reading frame of 353 amino acids and also encodes a transmembrane domain. [Blobel C. P., et al., Nature, 356, 248–251 (1992)]. The predicted amino acid sequence of the PH30 beta chain protein contains significant homology to a class of proteins called disintigrins found in snake venom. These proteins are known to bind to a family of proteins called integrins and prevent their normal functioning in cell adhesion (a well studied example is platelet aggregation). The N-terminal ninety amino acids integrin binding disintigrin domain of PH30 beta has been postulated to mediate the binding of PH30 to its putative integrin receptor on oocytes. The cloning and sequence determination of the mouse and human PH30 beta chain genes would permit novel approaches to the control of sperm egg binding and fusions. These approaches include, but are not limited to, eliciting an immune response directed at all or part of the PH30 beta chain protein and using the PH30 beta chain protein as part of a screen to identify small molecules that alter sperm egg interactions.

Mammalian fertilization is, in most cases, species specific. Thus, the identification and isolation of sperm surface proteins essential for fertilization in species other than guinea pig would be useful for providing effective long lasting contraception in those species. Thus far, the lack of biochemical identification, isolation and cloning of candidate adhesion proteins of sperm has hindered scientists in developing effective contraceptives for humans as well as other mammalian species.

SUMMARY OF THE INVENTION

The instant invention relates to a sperm protein in substantially pure form selected from a human PH30 beta chain protein, a mouse PH30 beta chain protein or an amino acid sequence substantially homologous to either the human or mouse PH30 beta chain protein.

In one embodiment of the invention is the sperm protein having an integrin binding sequence which is not TDE.

In one class is the sperm protein wherein the integrin binding sequence is selected from FEE or QDE.

In a subclass is the sperm protein which is the human PH30 beta chain protein.

Illustrative of this subclass is the sperm protein having an integrin binding sequence that is FEE.

Further illustrating the invention is a DNA sequence which encodes the sperm protein or a portion of the sperm protein sufficient to constitute at least one epitope.

An illustration is the DNA sequence wherein the epitope is on the native protein.

Exemplifying the invention is the DNA sequence which encodes all or a portion of human PH30 beta chain protein.

An example of the invention is the DNA sequence, wherein the DNA encoding all or a portion of the human PH30 beta protein is characterized by the ability to hybridize, under standard conditions, to the DNA sequence shown in SEQ ID NO: 1.

More particularly illustrating the invention is a contraceptive composition comprising a therapeutically effective amount of the protein, or a polypeptide having the substantially same amino acid sequence as a segment of the protein provided that the polypeptide is sufficient to constitute at least one epitope, and a pharmaceutically acceptable carrier.

Another illustration is the contraceptive composition wherein the epitope is on the native protein.

Further exemplifying the invention is the contraceptive composition, wherein the protein is the human PH30 beta chain protein.

More specifically illustrating the invention is the contraceptive composition, wherein the protein is produced by expressing the gene encoding an immunogenic epitope of the sperm protein in a recombinant DNA expression vector.

Specifically exemplifying the invention is a vector comprising an inserted DNA sequence encoding for the protein.

A further illustration of the invention is the vector, wherein the inserted DNA sequence is characterized by the ability to hybridize, under standard conditions, to a DNA sequence selected from the DNA sequences of SEQ ID NO: 1 or SEQ ID NO: 3.

Another example of the invention is a host that is compatible with and contains the vector.

More specifically exemplifying the invention is a method of producing a human or mouse PH30 beta chain sperm protein, comprising the steps of culturing cells containing PH30 beta chain DNA and recovering the sperm protein from the cell culture.

A further example is the method wherein the DNA encoding all or a portion of the PH30 beta chain protein is characterized by the ability to hybridize, under standard conditions, to a DNA sequence selected from the DNA sequences of SEQ ID NO: 1 or SEQ ID NO: 3.

A more specific illustration is a method of contraception in a human or mouse subject in need thereof, comprising administering to the subject an amount of the sperm protein which is effective for the stimulation of antibodies which bind to the sperm protein in vivo, thereby preventing or substantially reducing the rate of sperm-egg fusion.

Further illustrating the invention is the method wherein the sperm protein has an integrin binding sequence which is not TDE.

Another illustration is the PH30 beta chain protein made by the process described.

Another example is a DNA sequence as shown in Seq. ID No. 1 encoding human PH30 beta chain protein.

Still further illustrating the invention is a purified and isolated DNA sequence consisting essentially of a DNA sequence encoding a polypeptide having an amino acid sequence sufficiently duplicative of that of human or mouse PH30 beta to allow the possession of the biological property of initiating sperm-egg binding or promoting sperm-egg fusion. This biological activity can be determined using the in vitro sperm-oocyte binding/fusion assays [Primakoff, P., et al., *J. Cell. Biol.*, 104: 141–149 (1987)].

More particularly exemplifying the invention is the DNA sequence wherein the amino acid sequence contains an integrin binding sequence which is not TDE.

BRIEF DESCRIPTION OF THE DRAWINGS

FIGS. 1A, 1B, 1C, 1D, 1E, and 1G comprise a diagram representing the human PH30 beta cDNA gene sequence encoding the human PH-30 beta protein, and the deduced amino acid sequence of the human PH-30 beta protein present in three letter code. The sequence disclosure of FIGS. 1A through 1G is represented as SEQ ID NO: 1 and 2.

FIGS. 2A, 2B, 2C, 2D and 2E comprise a diagram representing the mouse PH30 beta cDNA gene sequence, and the deduced amino acid sequence of the mouse PH-30 beta protein present in three letter code. The sequence disclosure of FIGS. 2A through 2E is represented as SEQ ID NO: 3 and 4.

FIGS. 3A, 3B, 3C, 3D, 3E, 3G, 3H, 3I, 3J and 3K represent a restriction MAP of the human PH30 beta cDNA sequence.

FIGS. 4A, 4B, 4C, 4D, 4E, 4G and 4H represent a restriction MAP of the mouse PH30 beta cDNA sequence.

DETAILED DESCRIPTION OF THE INVENTION

The subject invention relates to sperm surface proteins which are essential for fertilization, or portions thereof, and their use in contraceptive methods. A sperm surface protein is essential for fertilization if, for example, a monoclonal antibody to the protein or a polyclonal antibody raised against the purified protein, when bound to sperm, inhibits in vitro or in vivo fertilization or any step of in vitro fertilization. The process of fertilization is defined as the binding or fusion of two gametes (sperm and egg) followed by the fusion of their nuclei to form the genome of a new organism. The surface protein can be located in the plasma membrane of sperm and/or the inner acrosomal membrane. It can be a protein or glycoprotein. The isolated surface protein used for immunization can comprise the entire surface protein or some portion of the protein (external to the cell) which is immunogenic. Two such sperm surface proteins are the mouse and human PH30 beta chain sperm surface proteins. The PH30 beta genes encode proteins which are present on the surface of sperm cells and are essential for fertilization.

As used herein, a protein or peptide is "substantially pure" when that protein or peptide has been purified to the extent that it is essentially free of other molecules with which it is associated in nature. The term "substantially pure" is used relative to proteins or peptides with which the peptides of the instant invention are associated in nature, and are not intended to exclude compositions in which the peptide of the invention is admixed with nonproteinous pharmaceutical carriers or vehicles.

As used herein, an amino acid sequence substantially homologous to a referent PH-30 beta protein will have at least 70% sequence homology, preferably 80%, and most preferably 90% sequence homology with the amino acid sequence of a referent PH-30 beta protein or a peptide thereof. For example, an amino acid sequence is substantially homologous to mouse PH-30 beta protein if, when aligned with mouse PH30 beta protein, at least 70% of its amino acid residues are the same. In addition, it is preferable that the substantially homologous amino acid sequence contains the integrin binding sequence.

As used herein, a DNA sequence substantially homologous to a referent PH-30 beta protein will have at least 70%, preferably 80%, and most preferably 90% sequence homology with the DNA sequence of a referent PH-30 beta. Moreover, a DNA sequence substantially homologous to a referent PH-30 beta protein is characterized by the ability to hybridize to the DNA sequence of a referent PH30 beta under standard conditions. Standard hybridization conditions are described in Maniatis, T., et al. (1989) Molecular Cloning, Cold Spring Harbor Laboratory, Cold Spring Harbor, N.Y.

An "expression vector" or "vector," as used herein, refers to a plasmid, bacteriophage, virus, or other molecule into which a gene of interest may be cloned, such that the appropriate signals for expression of that gene are present on that vector.

The term "epitope," as used herein, refers to the minimum amount of PH30 beta sequence capable of producing an efficacious, i.e., contraceptive, immune response.

The term "therapeutically effective amount," as used herein, means that amount of a drug or pharmaceutical agent that will elicit the biological or medical response that is being sought by a researcher or clinician.

Production and Purification of Immunogen

A preferred method for producing sperm surface proteins for use as a contraceptive immunogen is by recombinant DNA technology. To produce the protein using this technology it is necessary to isolate and clone DNA encoding the protein, or an immunogenic portion thereof. Those skilled in the art are familiar with a variety of approaches which can be used in an effort to clone a gene of interest. However, having nothing more than the isolated protein of interest, success in such an effort cannot be predicted with a reasonable degree of certainty.

In the Examples which follow, Applicants describe the cloning and characterization of the mouse and human PH30 beta chain genes. The mouse and human PH30 beta chain genes were isolated using a cDNA encoding the guinea pig PH30 beta chain gene. The instant invention provides specific sequence information to permit targeted intervention in controlling fertility through anti PH30 directed immune responses inhibition of sperm-egg binding and triggering of post binding signaling and effective events. These sequences permit the generation of reagents for the isolation of oocyte proteins involved in sperm-egg interaction.

The information presented in the Examples enable one skilled in the art to isolate and clone the mouse or human PH30 beta chain gene. For example, a cDNA library is prepared from testis or spermatogenic cells isolated from the mammal of interest (e.g., mouse, human). Such a cDNA library is then screened using, for example, labeled guinea pig PH30 DNA probes. DNA encoding all or a portion of human or mouse PH30 is characterized by the ability to hybridize to such a probe sequence under hybridization conditions such as those described in Example 1. Methods of labeling and screening by hybridization are well known in the art. Positive clones are analyzed. and a full length cDNA is constructed by conventional methods.

The cloned gene, or portions thereof which encode an immunogenic region of the PH30 protein, can be expressed by inserting the coding region into an expression vector to produce an expression construct. Many such expression vectors are known to those skilled in the art. These vectors contain a promoter for the gene of interest as well as additional transcriptional and translational signals. Expression vectors for both eukaryotic host cells and prokaryotic host cells are widely available. The DNA expression construct is used to transform an appropriate host cell.

Eukaryotic, in particular mammalian, host cells are often utilized for the expression of eukaryotic proteins. It has been found, for example, that eukaryotic proteins may exhibit folding problems when expressed in prokaryotic cells. In addition, production of authentic, biologically active eukaryotic proteins from cloned DNA sometimes requires post-translational modification such as disulfide bond formation, glycosylation, phosphorylation or specific proteolytic cleavage processes that are not performed in bacterial cells. This is especially true with membrane proteins. The sperm surface protein is produced using the transcriptional and translational components of the host cell. After an appropriate growth and expression period, the host cell culture is lysed and the sperm surface protein is purified from the lysate. Lysis buffers typically include non-ionic detergent, protease inhibitors, etc.

From the solubilized cell extract, the sperm surface protein can be purified and isolated by physical and biochemical methods such as ultracentrifugation, column chromatography, high performance liquid chromatography, electrophoresis, etc. Alternatively, the sperm surface protein can be isolated by affinity chromatography using monoclonal or polyclonal antibodies [see Primakoff et al., *Biol. of Reprod*. 38, 921–934 (1988)]. Such methods for purifying proteins are well known to those skilled in the art.

As mentioned above, antigenic portions or epitopes of the sperm surface protein are useful as immunogen, in addition to the full length protein. Antigenic fragments can be produced, for example, by proteolytic digestion of the full length protein, followed by isolation of the desired fragment. Alternatively, chemical synthesis can be used to generate the desired fragment starting with monomer amino acid residues.

With respect to the PH30 protein, certain antigenic domains are preferred candidates for use in a contraceptive vaccine. As is discussed in greater detail in the Exemplification section which follows, the PH30 β subunit contains a domain which is highly conserved when compared to a class of proteins known as disintegrins. A peptide (or portion thereof) which is identical or substantially identical to this domain is preferred for use in the contraceptive methods of this invention. Substantially identical, as used in the preceding sentence, means that at least 70% of the amino acid sequence of the peptide is identical to the corresponding portion of the PH30 β disintegrin domain.

Disintegrins are found in snake venom, for example, and are known to bind to a class of platelet surface proteins known as integrins. The binding of disintegrins to integrins has been shown to inhibit blood clotting. By analogy, peptides corresponding to the PH30 β disintegrin domain are predicted to be active in sperm-egg binding and fusion.

Contraceptive Vaccine

Once the sperm surface protein has been produced and purified, a vaccine can be produced by combining the sperm surface protein or portion thereof with a suitable carrier for administration to a subject for immunization. For successful vaccine development it is necessary that the immunogen exhibit tissue specificity, that is, it is expressed on the target tissue only and must be essential for the process of reproduction. It is known that the PH30 protein, which is expressed only on sperm, is involved in sperm egg binding and antibodies that bind to PH30 inhibit that interaction.

The cloning and characterization of human PH30 beta permits novel approaches for using PH30 as a target to control human fertility. PH30 beta protein or peptides can be used directly as an antigen to elicit an immune response directed to the whole or a relevant part of the PH30 beta chain protein. Testing of these approaches requires availability of sufficient quantities of PH30 beta protein. The cloning and sequencing of the mouse and human PH30 beta chain provides information necessary to recombinantly express all or part of the PH30 beta protein. These expressed proteins are used with or without adjuvant to immunize women or female mice. The elicited humoral immune responses are monitored by assays that use PH30 beta as antigen. Secreted antibodies in the female reproductive system will bind to the sperm head and disrupt fertilization. The availability of the recombinant mouse PH30 beta protein permits establishment of an animal model system for testing efficacy, reversibility and safety of specific methods of controlling fertility based on PH30.

A vaccine can contain one or more sperm surface proteins. Sperm surface proteins of the present invention can be combined with adjuvants which contain non-specific stimulators of the immune system. Proper use of adjuvants can induce a strong antibody response to foreign antigens (i.e., sperm surface proteins). The action of adjuvants is not fully understood, but most adjuvants incorporate two components. One is a substance designed to form a deposit which protects the antigen from catabolism. Two methods of forming a deposit are to use mineral oils or aluminum hydroxide precipitates. With mineral oils, such as Freund's adjuvant, the immunogen is prepared in a water-in-oil emulsion. For aluminum hydroxide, the immunogen is either adsorbed to preformed precipitants or is trapped during precipitation.

The second component required for an effective adjuvant is a substance that will stimulate the immune system non-specifically. These substances stimulate the production of a large set of soluble peptide factors known as lymphokines. In turn, lymphokines stimulate the activity of antigen-processing cells directly and cause a local inflammatory reaction at the site of injection. A component of lipopolysaccharide known as lipid A is commonly used. Lipid A is available in a number of synthetic and natural forms that are much less toxic than lipopolysaccharides, but still retain most of the desirable adjuvant properties of the lipopolysaccharide molecules. Lipid A compounds are often delivered using liposomes. The two bacteria that are commonly used in adjuvants as non-specific stimulants are Bordatella pertussis and Mycobacterium tuberculosis. When used as whole bacteria, they must be heat-killed prior to use. The imnmunomodulatory mediators of B. pertussis include a lipopolysaccharide component and the pertussis toxin. The pertussis toxin has been purified and is available commercially. M. tuberculosis is commonly found in complete Freund's adjuvant. The most active component of M. tuberculosis has been localized to muramyl dipeptide which is available in a number of forms.

Immunizations (Inoculation and Booster Shots)

The subject to be immunized can be any mammal which possesses a competent immune system. Examples of subject mammals include humans and domestic animals (e.g. dogs, cats, cows, horses, etc.), as well as animals intended for experimental or other purposes (e.g., mice, rats, rabbits, etc.).

Two different criteria are important to consider in determining the proper dose for the initial immunization. First, the optimum dose to achieve the strongest response and second, the minimum dose likely to induce the production of useful polyclonal antibodies. Much of the injected material will be catabolized and cleared before reaching the appropriate target immune cell. The efficiency of this process will vary with host factors, the route of injection, the use of adjuvants, and the intrinsic nature of the surface protein injected. Thus, the effective dose delivered to the immune system may bear little relationship to the introduced dose and consequently dose requirements must be determined empirically. These determinations can be readily made by one skilled in the art. Secondary injections and later boost can be given with amounts similar to or less than the primary injection.

The route of injection is guided by three practical decisions: 1) what volume must be delivered; 2) what buffers and other components will be injected with the immunogen; and 3) how quickly should the immunogen be released into the lymphatics or circulation. For example, with rabbits, large volume injections normally are given at multiple subcutaneous sites. For mice, large volumes are only possible with intraperitoneal injections. If adjuvants or particulate matter are included in the injection, the immunogen should not be delivered intravenously. If a slow release or the inoculant is desired, the injections should be done either intramuscularly or intradermally. For immediate release, use intravenous injections.

Primary antibody responses often are very weak, particularly for readily catabolized, soluble antigens. Hence, secondary or booster injections are required after the initial immunization. A delay is needed before reintroducing the protein into a primed subject. A minimum of 2 or 3 weeks is recommended but greater intervals are possible. The antibody responses to secondary and subsequent injections is much stronger. Higher titers of antibody are reached, but more importantly, the nature and quantity of the antibodies present-in serum changes. These changes yield high-affinity antibodies. The intervals between secondary, tertiary and subsequent injections may also be varied, but usually need to be extended to allow the circulating level of antibody to drop enough to prevent rapid clearance of newly injected antigen.

Subsequent booster injections will be required to increase reduced circulating antibody for continued contraception. The actual intervals for these injections will differ from species to species. However, the intervals can be determined by one skilled in the art by monitoring serum levels of sperm surface protein antibodies.

In another embodiment, subjects can be administered with alloantisera, or monoclonal antibodies, directed to a sperm surface protein to achieve contraception. The alloantiserum is raised in another individual of the same species, isolated from the serum of the individual and prepared in a suitable carrier for injection into the recipient subject. Those skilled in the art are familiar with methods for preparing and formulating monoclonal antibodies for administration.

There is convincing evidence that naturally occurring antibodies to sperm cause infertility in women [Bronson, R. A., et al., Fertility and Sterility, 42: 171–183 (1984)]. This infertility is better correlated with the antibody titers in cervical mucus than with the serum [Clark, G. N., Amer. J Reprod. Immunol., 5:179–181 (1984)]. Presence of anti-sperm antibodies in the cervical mucus of infertile women results in poor sperm penetration through the cervical mucus and agglutination of the sperm, thereby reducing the number of sperm available for fertilization. Thus, success of a contraceptive vaccine depends in particular on the generation of mucosal immune responses involving sustained titers of antisperm antibodies in the female reproductive tract.

Generally, local application of the antigen is an effective way to stimulate an antibody response by that mucosa [Mestecky, J., J Clin. Immunol., 7: 265–276 (1987)]. However, local mucosal immunization is ineffective in female reproductive tract due to the barrier function of the luminal epithelium and to rapid loss of antigen from the lumen of reproductive tract. Stability and adhesiveness of the antigen on the mucosal surface is important for the induction of the mucosal immune responses [de Aizpurua, H. J. and Russell-Jones, G. J., J Exp. Med., 167: 440 (1988)]. Adhesive antigens are critical to successful mucosal immunization, not only because they are effective mucosal immunogens themselves, but also because they are carrier proteins for other antigens. Cholera toxin is a potent immunogen when given mucosally, but acts as an adjuvant when given in combination with other antigens [McKenzie, S. J. and Halsey, J. A., J. Immunol., 133: 1818 (1984)]. Effective immunization is also dependent on the stability of the antigen on a mucosal surface. Many antigens for use in mucosal vaccines are poorly immunogenic because they are unable to survive in the acidic and proteolytic conditions of the mucosal surface [O'Hagen, D. T., Curr. Opin. Infect. Dis., 3:393 (1990)]. The DL-lactide-co-glycolide (DL-PLG) microsphere, microparticle carrier system is one of the most suitable systems for mucosal immunization. DL-PLG microspheres protect the antigen at mucosal surface and are taken up by the mucosal lymphoid tissues where they induce mucosal immunity [Eldridge, J. H. et al, Curr. Top. Microbiol. Immunol., 146: 59 (1989)]. Liposomes and inactivated micro-organisms also are used as microparticle carriers. Some parenteral adjuvants such as Avridine, a lipoidal amine and muramyl dipeptide (MDP), the active component of mycobacteria in Freund's complete adjuvant, also have been shown to be active as oral mucosal adjuvants and enhance mucosal immunization [Anderson, A. O. and Reynolds, J. A., *J. Reticuloendothel. Soc.*, 26(suppl): 667 (1979); Taubman, M. A., et al., *Ann. NY Acad. Sci.*, 409: 637 (1983)]. Development of mucosal immune responses in female reproductive tract are optimized by using various adjuvants, micro particle carriers, by immunizing at local or remote mucosal surfaces or by combination of parenteral and mucosal immunization.

Utility of PH30 beta in Identification of Small Molecules that will Disrupt Sperm-erg Interaction and Fertilization The comparison of the protein sequences of both mouse and human PH30 beta chain genes shows significant homology to a class of proteins called disintegrins found in the snake venoms. These proteins are known to bind a family of cell surface molecules called integrins and prevent their normal function in cell adhesion. On the basis of these homologies it is reasonable to conclude that the PH30 receptor on the oocyte is an integrin. Comparisons of the disintegrin domain sequences of guinea pig, mouse and human PH30 beta chain genes show significant differences in their putative ligand binding domain. In particular, the sequences in this region are different from other disintegrins and among the three species. The recombinant mouse and human PH30 beta proteins are used to make affinity resins to purify, identify and characterize mouse and human PH30 receptors. The recombinant PH30 beta also are used to determine its relative affinity to other integrins expressed in other tissues and are used as a ligand for cloning of the PH30 receptor.

Since the integrin recognition sequences in PH30 beta are species specific, the sequence information is necessary to identify small molecules that disrupt fertilization in a species specific manner. The recombinant mouse and human PH30 beta are used to set up screens to identify small molecules that act either as antagonist to PH30 receptor and disrupt PH30 binding or act as an agonist and stimulate PH30 receptor inducing transmembrane signaling, egg cortical granule release and zona reaction thus making the egg impenetrable for fertilization.

The present invention is further illustrated in the following exemplification.

EXAMPLE 1

Isolation of DNA Encoding Mouse and Human PH30 beta

A. cDNA Library Plating

One million independent recombinant bacteriophage from both a human testis cDNA library in λgt 11 (Clontech, Palo Alto, Calif.) and mouse testis cDNA library (Stratagene La Jolla, Calif.) in UNI-ZAP XR were plated. Plaque lifts were done in duplicate by placing a nitrocellulose filter on the plate for two minutes, and treating the filter with denaturing solution (0.5M NaOH, 1.5M NaCl), neutralization buffer (0.5M Tris pH 7.5, 1.5M NaCl) and 2× SSC (3M NaCl, 0.35M sodium citrate pH 7.0) for two minutes each. The filters were dried for thirty minutes at room temperature and then baked for two hours at 80° C. in a vacuum oven.

B. Generation of Probe:

A guinea pig PH30 beta cDNA was isolated by RT-PCR (reverse transcriptase-polymerase chain reaction) as a 1020 bp (base pairs), HindIII/Bam HI fragment, containing 94% of the coding sequence. This fragment was subcloned into pBluescript SK+ vector (Stratagene, La Jolla, Calif.) and verified by sequence analysis. A probe was made by nick translating the purified 1020 bp guinea pig PH30 beta fragment. The filters were probed at 42° C. for fifteen hours in hybridization solution (7 mM Tris pH 7.5, 40% formamide, 4× SSC, 0.8× Denhard's, 20 μg/ml of salmon sperm DNA and 10% Dextran sulfate) containing $10^6$ cpm (counts per minute)/ml of the labeled probe. The filters were washed twice at room temperature for fifteen minutes each with 2× SSC/0.2% SDS (sodium dodecyl sulfate), then twice at room temperature with 0.2× SSC/0.1%SDS, then once at 42° C. for 30 minutes with 0.1× SSC/0.1%SDS. The filters were exposed to XAR film (Eastman Kodak Co, Rochester, N.Y.) for 15 hours. The positive plaques were picked into 1 ml of SM (0.1M NaCl, 10 mM Magnesium Sulphate, 2% gelatin, 50 mM Tris pH 7.5) and screened again as described above. After four rounds of screening, the purified plaques were obtained.

Purified plaques of mouse testicular library were subcloned into pBluescript SK+ vector using the EX ASSIT helper phage and SOLR cells (Stratagene, La Jolla, Calif.). DNA from the purified plaques of human testicular library was isolated using light PLG 2 tubes and following manufacturer's (Clontech, Palo Alto, Calif.) directions. The DNA was then digested with the restriction enzyme EcoRI and ligated into pBluescript SK+ and was used to transform competent *E. coli* strain HB101 cells.

C. DNA Sequencing and Analysis:

Cloned inserts were sequenced on both strands using the Sequenase kit (United States Biochemical, Cleveland, Ohio). Sequences were analyzed by searching GeneBank and EMBL DNA sequence database using the FASTA program (University of Wisconsin, Genetics Computer Group) and sequence comparisons were done using the GAP program.

D. Characterization of cDNA Clones:

The screening of the mouse testicular library with a 1020 bp guinea pig PH30 beta probe resulted in the isolation of a 1.7 kb (kilo base pair) cDNA clone. This cDNA clone contains a 1371 nucleotide open reading frame and a 329 nucleotide 3' untranslated region. When mature parts of the guinea pig and mouse PH30 beta were compared, the mouse PH30 beta clone showed a maximum of 63% identity to guinea pig PH30 beta at the nucleotide level. The amino terminal 103 residues of the deduced 457 amino acid sequence represents the precursor regions of the mouse PH30 beta that are cleaved off at sperm maturation. At the amino acid level the mature mouse, and guinea pig PH30 betas were 54% identical with all the cysteines lining up.

The human testicular cDNA library screening identified a 2.331 kb cDNA which contains an open reading frame of 1959 nucleotides and 372 nucleotide 3' untranslated region. The human PH30 beta clone was 63 and 67% identical in its open reading frame to mouse and guinea pig PH30 beta genes, respectively. Comparison of the derived 653 amino acid sequence with the mouse and guinea pig PH30 beta indicates that the amino terminal 299 represents the precursor and carboxy terminal 354 amino acids represent the mature part of human PH30 beta respectively. The amino acid sequence of the mature human PH30 beta was 54% homologous to mature guinea pig and mouse PH30 beta proteins.

Protein sequence comparison of mouse and human PH30 beta to guinea pig PH30 beta and snake venom disintegrins indicated significant homology. This analysis revealed similar structural organization and indicated the presence of metalloprotease and disintegrin domains in these proteins.

Metalloprotease domains of mouse and human PH30 beta shared significant similarity with the metalloprotease domains of guinea pig PH30 beta but less similarity to the metalloprotease domain of guinea pig PH30 alpha or other disintegrins. The active site signature sequence of zinc-dependent metalloproteases is present in PH30 alpha and the snake venom disintegrins, Jararhagin and Trigramin. [Wolfsberg, T. G., et al., Proc. Natl. Acad. Sci. USA 90: 10783–10797 (1 993)]. Similar to guinea pig PH30 beta, the mouse and human metalloprotease domain lacks the active site signature sequence and both were 80% identical to guinea pig PH30 beta and only 30% identical to guinea pig PH30 alpha metalloprotease active site sequence. Human and guinea pig PH30 beta metalloprotease domains were 60% identical.

Similar to guinea pig PH30 beta, the mouse and human PH30 beta also contain a disintegrin domain. The disintegrin domain in mouse PH30 beta contains 91 amino acids (residues 111–202) and in human, 93 amino acids (residues 299–392). Most disintegrins of snake venom contain a consensus integrin binding sequence RGD. Another family of snake venom disintegrins that are linked to a carboxyl terminus cysteine rich domain, lack the RGD tripeptide but contain a unique tripeptide and adjacent cysteine. Guinea pig, mouse and human PH30 beta proteins also do not contain RGD tripeptide and share more similarity with this later family of disintegrins. These snake venom disintegrins and disintegrin domains of guinea pig, mouse and human PH30 beta contain a negatively charged residue at the carboxyl end of the tripeptide sequence. The integrin binding sequence of guinea pig PH30 beta is TDE. One skilled in the art would have expected that the integrin binding site of PH30 beta of other mammalian species would also be TDE. However, after isolation of human and mouse PH30 beta, it was found that this was not the case. It was unexpectedly discovered that the critical sequence at the integrin binding site was not conserved. Comparisons of guinea pig, mouse and human PH30 beta disintegrin domains showed significant variation in their putative integrin binding sequences although the carboxy terminus end of these domains were identical. The putative integrin binding residues in PH30 beta were QDE in mouse and FEE in human. These differences in the integrin binding sequences between species were an unexpected and surprising finding.

Both mouse and human PH30 beta contain an epidermal growth factor like repeat and a transmembrane domain that are 60% identical to similar regions of guinea pig PH30 beta.

EXAMPLE 2
Cloning of the 5' end of Mouse and Human PH30 Beta

The 5' ends of mouse and human PH30 beta were cloned using the Gibco BRL "5' RACE System for Rapid Amplification of cDNA Ends" and following manufacturer's protocols. 2 oligonucleotides were synthesized for each template. Oligo 1 was an antisense primer and Oligo 2 was also an antisense primer, internal to oligo 1, and contained in the CAU sequences on the 5' end to facilitate cloning. Oligo 1 was annealed to mouse or human testis mRNA and a cDNA copy was made using SuperScript II Reverse Transcriptase. The MRNA template was degraded with Rnase H. The single strands cDNA copy was purified with GlassMAX Spin columns and was then tailed on the 3' end with dCTP and terminal transferase. The tailed cDNA copy was then amplified using a supplied anchor primer that contains the 5' CAU cloning site and oligo 2. The amplification system was Taq polymerase. The amplified product was then gel purified, treated with Uracil DNA Glycosylase, subcloned into the vector pAMP1 and then transformed into competent E. coli DH5 cells. Colonies were identified which had subcloned fragment and these colonies were sequenced as described previously.

The complete mouse cDNA sequence and the deduced amino acid sequence of the mouse PH30 beta protein is shown in SEQ ID NO: 5 and SEQ ID NO: 6. The complete human cDNA sequence and the deduced amino acid sequence of the human PH30 beta protein is shown in SEQ ID NO: 7 and SEQ ID NO: 8.

At the nucleotide level, the complete human PH30 beta shares 68% identity with mouse and 68.6% identity with guinea pig PH30 beta, respectively. Mouse and guinea pig DNA sequences are 65.5% identical. The amino acid sequence of the human PH30 beta is 58.9% identical to mouse and 56.5% identical to guinea pig PH30 beta. At the amino acid level, the mouse and guinea pig PH30 beta are 55.2% identical.

EXAMPLE 3
Contraceptive Vaccination by the Administration of PH30 beta Protein

Female or male mice (about 7 weeks old at the time of first injection) receive two injections of PH30 beta in the amounts stated below. Recombinant or native PH30 beta, purified from cell line or sperm by mAb-affinity chromatography or biochemical methods, shows at least 90% purity (i.e., no more than 10% detectable contaminants) using silver-staining of purified protein on SDS gels. Purity of each PH30 preparation used for immunization of females or males is verified by SDS polyacrylamide gel electrophoresis and silver staining. The affinity-purified PH30 beta, in 0.375 ml phosphate-buffered saline (PBS) containing 3 mM octyglucoside (OG) is emulsified with 0.375 ml complete Freund's adjuvant (CFA). Each animal receives 0.1 ml of the emulsion subcutaneously in the back and 0.05 ml intramuscularly in a rear leg. About 3 weeks later, the same amount of PH30 beta in PBS and 3 mM OG is emulsified with incomplete Freund's adjuvant (IFA), and is injected in the same sites in each animal. Control females and males receive the same injections on the same schedule and containing PBS and 3 mM OG and CFA or IFA, but lacking PH30 beta. To allow the injected females to mate, about 6 weeks after the initial injection they are housed with males for 10 days. Each cage contains one male (13 weeks old), one PH30 beta immunized female, and from 2–4 control injected females. 24 hours after the grouping, females are checked visually daily for the vaginal plugs. Two weeks after the initiation of the mating the, females are removed into individual cages. After three weeks the pregnant females having litters and progeny are counted. To allow the injected males to mate, about six weeks after the initial injection, each injected male is housed with two females (10–13 weeks) for 10 days. The females and males are then separated and after an additional 3 weeks pups are counted.

EXAMPLE 4
Use of PH30 Disintegrin Peptides as Inhibitor of Sperm Fusion to Egg Plasma Membrane Peptides from the PH30 β disintegrin domain are tested for inhibition of sperm binding to the egg plasma membrane.

The fusion inhibition assay is carried out as follows. Young female mice (8–10 weeks of age) are injected with 5 units of pregnant mare's serum (PMS) in 0.9 NaCl intraperitoneally. 48 hours later, the mice are injected IP with 5 units of hCG (human chorionic gonadotrophin) in 0.9% NaCl to trigger super ovulation. 14–16 hours after hCG injection, the ovulated oocytes are collected and treated with hyaluronidase to remove cumulus cells. The zona pellucida is removed with a mixture of proteases. The zona pellucida free eggs are incubated in culture media with peptide at a specified concentration for 30 minutes [Hogan, B., et al., Manipulating The Mouse Embryo, 91–101, (1986)]. Sperm collected from the epididymis of male mice is capacitated by incubation and acrosome reacted as described by Fleming and Yanagimachi [*Gamete Res.* 4, 253–273 (1981)] and added to the eggs and incubated for 15 minutes. The eggs are then transferred to a sperm free culture medium and incubated for an additional 1 hour and 45 minutes. The eggs are then fixed and stained as described by Primakoff et al., [*J. Cell. Biol.* 104, 141 (1987)]. The total number of swollen sperm heads are then counted. Swollen sperm heads are an indication that the sperm and egg have fused.

On the basis of these observations, several indices are calculated. The fertilization index (F.I.) is determined by dividing the total number of swollen heads by the total number of eggs. The fertilization rate (F.R.) is the percentage of eggs fertilized. The percent inhibition is determined by dividing the fertilization index of the experimental peptide by the fertilization index of the control peptide.

The PH30 β disintegrin domain represents an epitope which is critical in sperm-egg fusion. Antibodies which bind specifically to this epitope block sperm/egg fusion.

EXAMPLE 5
Use of PH30 beta to Identify Small Molecules that will disrupt sperm-egg Interaction and Fertilization A. Identification of PH30 beta receptor antagonists:

Identification of compounds that specifically interfere with the binding of PH30 to their receptor on the egg, has been limited due to unavailability of the sufficient quantities of PH30 protein and normal human eggs. The availability of the rPH30 beta facilitates the identification and cloning of PH30 beta receptor integrin cDNAs. These PH30 beta receptor cDNAs are used to generate recombinant PH30 beta receptors. The alternative source of PH30 beta receptors facilitates identification of substances that affect the binding of PH30 beta to its receptors.

Using conventional methods, the Chinese Hamster Ovary cells are transfected with cDNAs encoding the PH30 beta receptor to produce a stable transformed cell which expresses human PH30 beta receptor integrin in large quantities. Such a transformed cell provides a consistent source of recombinant PH30 beta receptors and is useful in the characterization of the binding of PH30 beta to its receptor and for establishing assays to screen for compounds that inhibit PH30 binding to its receptor.

Selectivity of the compounds to PH30 beta receptor is examined by using cell lines that express other integrin receptors that contain the same beta subunit and closely related alpha chain. Compounds that specifically inhibit PH30 beta/receptor interaction are tested further in biological assays, like inhibition of sperm-egg fusion assay and egg cortical granule release assay to determine their efficacy in inhibiting fertilization.

B. Protocol for PH30 beta antagonist screen:

Cells expressing PH30 beta receptor are treated with extraction buffer (50 mM Tris pH 7.6, 100 mM n-Octyl β-D-Glucopyranoside, 150 mM NaCl, 1 mM $MgCl_2$ and 1 mM $CaCl_2$) and soluble material is separated by centrifugation and stored frozen at −80° C. In an assay tube the 15 µl water, 80 µl of assay buffer (125 mM Tris pH 7.6, 187.5 mM NaCl, 1.25 mM $CaCl_2$, 1.25 mM $MgCl_2$ and 1.25% BSA) and 5 µl of sample compound or control (40 µM of cold PH30 beta) are added and mixed with 50 µl of $^{125}$I-PH30 beta (final concentration 40 pM) and 50 µl of cell extract (final protein concentration 250 µg/ml). The tubes are incubated at room temperature for 1 hour. Following incubation the samples are harvested using Tomtec Mach II-6× 16 cell harvester and printed filtermat cat. # 1205–404. Filters are dried and counted in LKB/Wallac Beta Plate counter. Calculations and Interpretations:

$$\% \text{ Inhibition} = \frac{CPMavg \text{ total binding} - CPMavg \text{ sample}}{CPMavg \text{ total binding} - CPMavg \text{ positive control}} \times 100$$

When % inhibition >60 and the inhibition is dose related, the sample will be considered active.

C. Sperm-Oocyte fusion assay:

Young female mice (approximately 8–10 weeks of age) are injected with 5 units of pregnant mare's serum (PMS) in 0.9 NaCl intraperitoneally. 48 hours later, the mice are injected IP with 5 units of hCG (human chorionic gonadotrophin) in 0.9% NaCl to trigger super ovulation. 14–16 hours after hCG injection, the ovulated oocytes are collected and treated with hyaluronidase to remove cumulus cells. Zona pellucida is removed by treating eggs briefly with 0.1 mg/ml of chymotrypsin. Oocytes are washed with Hepes buffered culture medium and are loaded with a fluorescent stain 4',6-diamidino-2-phenylindole dihydrochloride (DAPI) by incubating at 37° C. for 30 minutes. Oocytes are then washed with medium and incubated with rPH30 beta or inhibitor compound for 30 minutes followed by another 30 minute incubation with $1 \times 10^4$ sperms that have been previously capacitated by incubating with calcium ionophore. After incubation, the oocytes are washed, mounted and examined by light microscopy and scored for the presence of fluorescent swollen sperm heads with associated tails in cytoplasm.

$$\text{Fertilization rate} = \frac{\text{number of eggs fused}}{\text{number of eggs tested}} \times 100 \text{ (results expressed as \% fertilization)}$$

In the absence of any inhibitor >90% oocytes are fertilized. When the sperm-oocyte fusion is inhibited >60% and the inhibition is dose related the compound will be considered active.

While the invention has been described and illustrated with reference to certain preferred embodiments thereof, those skilled in the art will appreciate that various changes, modifications and substitutions can be made therein without departing from the spirit and scope of the invention. It is intended, therefore, that the invention be limited only by the scope of the claims which follow and that such claims be interpreted as broadly as is reasonable.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 2373 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:1:

```
GGCCAAGATT TTCAGAATTT CTGCCACTAC CAAGGGTATA TTGAAGGTTA TC
CAAAATCT     60

GTGGTGATGG TTAGCACATG TACTGGACTC AGGGGCGTAC TACAGTTTGA AA
ATGTTAGT    120

TATGGAATAG AACCCCTGGA GTCTTCAGTT GGCTTTGAAC ATGTAATTTA CC
AAGTAAAA    180

CATAAGAAAG CAGATGTTTC CTTATATAAT GAGAAGGATA TTGAATCAAG AG
ATCTGTCC    240

TTTAAATTAC AAAGCGCAGA GCCACAGCAA GATTTTGCAA AGTATATAGA AA
TGCATGTT    300

ATAGTTGAAA AACAATTGTA TAATCATATG GGGTCTGATA CAACTGTTGT CG
CTCAAAAA    360

GTTTTCCAGT TGATTGGATT GACGAATGCT ATTTTTGTTT CATTTAATAT TA
CAATTATT    420

CTGTCTTCAT TGGAGCTTTG GATAGATGAA AATAAAATTG CAACCACTGG AG
AAGCTAAT    480

GAGTTATTAC ACACATTTTT AAGATGGAAA ACATCTTATC TTGTTTTACG TC
CTCATGAT    540

GTGGCATTTT TACTTGTTTA CAGAGAAAAG TCAAATTATG TTGGTGCAAC CT
TTCAAGGG    600

AAGATGTGTG ATGCAAACTA TGCAGGAGGT GTTGTTCTGC ACCCCAGAAC CA
TAAGTCTG    660

GAATCACTTG CAGTTATTTT AGCTCAATTA TTGAGCCTTA GTATGGGGAT CA
CTTATGAT    720

GACATTAACA AATGCCAGTG CTCAGGAGCT GTCTGCATTA TGAATCCAGA AG
CAATTCAT    780

TTCAGTGGTG TGAAGATCTT TAGTAACTGC AGCTTCGAAG ACTTTGCACA TT
TTATTTCA    840

AAGCAGAAGT CCCAGTGTCT TCACAATCAG CCTCGCTTAG ATCCTTTTTT CA
AACAGCAA    900

GCAGTGTGTG GTAATGCAAA GCTGGAAGCA GGAGAGGAGT GTGACTGTGG GA
CTGAACAG    960

GATTGTGCCC TTATTGGAGA ACATGCTGT GATATTGCCA CATGTAGATT TA
AAGCCGGT   1020

TCAAACTGTG CTGAAGGACC ATGCTGCGAA AACTGTCTAT TTATGTCAAA AG
AAAGAATG   1080

TGTAGGCCTT CCTTTGAAGA ATGCGACCTC CCTGAATATT GCAATGGATC AT
CTGCATCA   1140

TGCCCAGAAA ACCACTATGT TCAGACTGGG CATCCGTGTG GACTGAATCA AT
GGATCTGT   1200

ATAGATGGAG TTTGTATGAG TGGGGATAAA CAATGTACAG ACACATTTGG CA
AGAAGTA    1260

GAGTTTGGCC CTTCAGAATG TTATTCTCAC CTTAATTCAA AGACTGATGT AT
CTGGAAAC   1320
```

-continued

```
TGTGGTATAA GTGATTCAGG ATACACACAG TGTGAAGCTG ACAATCTGCA GT
GCGGAAAA      1380

TTAATATGTA AATATGTAGG TAAATTTTTA TTACAAATTC CAAGAGCCAC TA
TTATTTAT      1440

GCCAACATAA GTGGACATCT CTGCATTGCT GTGGAATTTG CCAGTGATCA TG
CAGACAGC      1500

CAAAAGATGT GGATAAAAGA TGGAACTTCT TGTGGTTCAA ATAAGGTTTG CA
GGAATCAA      1560

AGATGTGTGA GTTCTTCATA CTTGGGTTAT GATTGTACTA CTGACAAATG CA
ATGATAGA      1620

GGTGTATGCA ATAACAAAAA GCACTGTCAC TGTAGTGCTT CATATTTACC TC
CAGATTGC      1680

TCAGTTCAAT CAGATCTATG GCCTGGTGGG AGTATTGACA GTGGCAATTT TC
CACCTGTA      1740

GCTATACCAG CCAGACTCCC TGAAAGGCGC TACATTGAGA ACATTTACCA TT
CCAAACCA      1800

ATGAGATGGC CATTTTTCTT ATTCATTCCT TTCTTTATTA TTTTCTGTGT AC
TGATTGCT      1860

ATAATGGTGA AAGTTAATTT CCAAAGGAAA AAATGGAGAA CTGAGGACTA TT
CAAGCGAT      1920

GAGCAACCTG AAAGTGAGAG TGAACCTAAA GGGTAGTCTG GACAACAGAG AT
GCCATGAT      1980

ATCACTTCTT CTAGAGTAAT TATCTGTGAT GGATGGACAC AAAAAAATGG AA
AGAAAAGA      2040

ATGTACATTA CCTGGTTTCC TGGGATTCAA ACCTGCATAT TGTGATTTTA AT
TTGACCAG      2100

AAAATATGAT ATATATGTAT AATTTCACAG ATAATTTACT TATTTAAAAA TG
CATGATAA      2160

TGAGTTTTAC ATTACAAATT TCTGTTTTTT TAAAGTTATC TTACGCTATT TC
TGTTGGTT      2220

AGTAGACACT AATTCTGTCA GTAGGGGCAT GGTATAAGGA AATATCATAA TG
TAATGAGG      2280

TGGTACTATG ATTAAAAGCC ACTGTTACAT TCAAAAAAA AAAAAAAAAA AC
CATCTAAA      2340

AAAGGTAGGT AGGTAAAAGA ATTATATTAT CAA
         2373
```

(2) INFORMATION FOR SEQ ID NO:2:

(i) SEQUENCE CHARACTERISTICS:
        (A) LENGTH: 651 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Gly Gln Asp Phe Gln Asn Phe Cys His Tyr Gln Gly Tyr Ile Glu Gly
 1               5                  10                  15

Tyr Pro Lys Ser Val Val Met Val Ser Thr Cys Thr Gly Leu Arg Gly
                20                  25                  30
```

-continued

Val Leu Gln Phe Glu Asn Val Ser Tyr Gly Ile Glu Pro Leu Glu Ser
                35          40          45

Ser Val Gly Phe Glu His Val Ile Tyr Gln Val Lys His Lys Lys Ala
    50              55              60

Asp Val Ser Leu Tyr Asn Glu Lys Asp Ile Glu Ser Arg Asp Leu Ser
65              70              75              80

Phe Lys Leu Gln Ser Ala Glu Pro Gln Gln Asp Phe Ala Lys Tyr Ile
                85          90          95

Glu Met His Val Ile Val Glu Lys Gln Leu Tyr Asn His Met Gly Ser
                100         105         110

Asp Thr Thr Val Val Ala Gln Lys Val Phe Gln Leu Ile Gly Leu Thr
            115         120         125

Asn Ala Ile Phe Val Ser Phe Asn Ile Thr Ile Ile Leu Ser Ser Leu
        130         135         140

Glu Leu Trp Ile Asp Glu Asn Lys Ile Ala Thr Thr Gly Glu Ala Asn
145                 150                 155                 160

Glu Leu Leu His Thr Phe Leu Arg Trp Lys Thr Ser Tyr Leu Val Leu
                165         170         175

Arg Pro His Asp Val Ala Phe Leu Leu Val Tyr Arg Glu Lys Ser Asn
            180         185         190

Tyr Val Gly Ala Thr Phe Gln Gly Lys Met Cys Asp Ala Asn Tyr Ala
        195         200         205

Gly Gly Val Val Leu His Pro Arg Thr Ile Ser Leu Glu Ser Leu Ala
    210         215         220

Val Ile Leu Ala Gln Leu Leu Ser Leu Ser Met Gly Ile Thr Tyr Asp
225                 230                 235

```
                    40
Asp Ile Asn Lys Cys Gln Cys Ser Gly Ala Va
l Cys Ile Met Asn Pro
                245
                    250
                        255

Glu Ala Ile His Phe Ser Gly Val Lys Ile Ph
e Ser Asn Cys Ser Phe
                260
                    265
                        270

Glu Asp Phe Ala His Phe Ile Ser Lys Gln Ly
s Ser Gln Cys Leu His
            275
                280
                    285

Asn Gln Pro Arg Leu Asp Pro Phe Phe Lys Gl
n Gln Ala Val Cys Gly
        290
            295
                300

Asn Ala Lys Leu Glu Ala Gly Glu Glu Cys As
p Cys Gly Thr Glu Gln
305                 3
    10                  3
        15                  3
            20

Asp Cys Ala Leu Ile Gly Glu Thr Cys Cys As
p Ile Ala Thr Cys Arg
                325
                    330
                        335

Phe Lys Ala Gly Ser Asn Cys Ala Glu Gly Pr
o Cys Cys Glu Asn Cys
                340
                    345
                        350

Leu Phe Met Ser Lys Glu Arg Met Cys Arg Pr
o Ser Phe Glu Glu Cys
            355
                360
                    365

Asp Leu Pro Glu Tyr Cys Asn Gly Ser Ser Al
a Ser Cys Pro Glu Asn
        370
            375
                380

His Tyr Val Gln Thr Gly His Pro Cys Gly Le
u Asn Gln Trp Ile Cys
385                 3
    90                  3
        95                  4
            00

Ile Asp Gly Val Cys Met Ser Gly Asp Lys Gl
n Cys Thr Asp Thr Phe
                405
                    410
                        415

Gly Lys Glu Val Glu Phe Gly Pro Ser Glu Cy
s Tyr Ser His Leu Asn
                420
                    425
                        430

Ser Lys Thr Asp Val Ser Gly Asn Cys Gly Il
e Ser Asp Ser Gly Tyr
                435
                    440
```

```
            445

Thr Gln Cys Glu Ala Asp Asn Leu Gln Cys Gl
y Lys Leu Ile Cys Lys
    450
        455
            460

Tyr Val Gly Lys Phe Leu Leu Gln Ile Pro Ar
g Ala Thr Ile Ile Tyr
465             4
70              4
75              4
80

Ala Asn Ile Ser Gly His Leu Cys Ile Ala Va
l Glu Phe Ala Ser Asp
            485
                490
                    495

His Ala Asp Ser Gln Lys Met Trp Ile Lys As
p Gly Thr Ser Cys Gly
            500
                505
                    510

Ser Asn Lys Val Cys Arg Asn Gln Arg Cys Va
l Ser Ser Ser Tyr Leu
        515
            520
                525

Gly Tyr Asp Cys Thr Thr Asp Lys Cys Asn As
p Arg Gly Val Cys Asn
    530
        535
            540

Asn Lys Lys His Cys His Cys Ser Ala Ser Ty
r Leu Pro Pro Asp Cys
545                 5
50                  5
55                  5
60

Ser Val Gln Ser Asp Leu Trp Pro Gly Gly Se
r Ile Asp Ser Gly Asn
            565
                570
                    575

Phe Pro Pro Val Ala Ile Pro Ala Arg Leu Pr
o Glu Arg Arg Tyr Ile
            580
                585
                    590

Glu Asn Ile Tyr His Ser Lys Pro Met Arg Tr
p Pro Phe Phe Leu Phe
        595
            600
                605

Ile Pro Phe Phe Ile Ile Phe Cys Val Leu Il
e Ala Ile Met Val Lys
    610
        615
            620

Val Asn Phe Gln Arg Lys Lys Trp Arg Thr Gl
u Asp Tyr Ser Ser Asp
625             6
30              6
35              6
40

Glu Gln Pro Glu Ser Glu Ser Glu Pro Lys Gl
y
            645
```

650

(2) INFORMATION FOR SEQ ID NO:3:

(i) SEQUENCE CHARACTERISTICS:
        (A) LENGTH: 1768 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
GGCACGAGCG ATTATGTTGG CGCTACCTAT CAAGGGAAGA TGTGTGACAA GA
ACTATGCA         60

GGAGGAGTTG CTTTGCACCC CAAAGCCGTA ACTCTGGAAT CACTTGCAAT TA
TTTTAGTT        120

CAGCTGCTGA GCCTCAGCAT GGGGCTAGCG TATGACGACG TGAACAAGTG CC
AGTGTGGC        180

GTACCTGTCT GCGTGATGAA CCCGGAAGCG CCTCACTCCA GCGGTGTCCG GG
CCTTCAGT        240

AACTGCAGCA TGGAGGACTT TTCCAAGTTT ATCACAAGTC AAAGCTCCCA CT
GTCTGCAG        300

AACCAGCCAA CGCTACAGCC ATCTTACAAG ATGGCGGTCT GTGGGAATGG AG
AGGTGGAA        360

GAAGATGAAA TTTGCGACTG TGGAAAGAAG GGCTGTGCAG AAATGCCCCC GC
CATGCTGT        420

AACCCCGACA CCTGTAAGCT GTCAGATGGC TCCGAGTGCT CCAGCGGGAT AT
GCTGCAAC        480

TCGTGCAAGC TGAAGCGGAA AGGGGAGGTT TGCAGGCTTG CCCAAGATGA GT
GTGATGTC        540

ACAGAGTACT GCAACGGCAC ATCCGAAGTG TGTGAAGACT TCTTTGTTCA AA
ACGGTCAC        600

CCATGTGACA ATCGCAAGTG GATCTGTATT AACGGCACCT GTCAGAGTGG AG
AACAGCAG        660

TGCCAGGATC TATTTGGCAT CGATGCAGGC TTTGGTTCAA GTGAATGTTT CT
GGGAGCTG        720

AATTCCAAGA GCGACATATC TGGGAGCTGT GGAATCTCTG CTGGGGATA CA
AGGAATGC        780

CCACCTAATG ACCGGATGTG TGGGAAAATA ATATGTAAAT ACCAAAGTGA AA
ATATACTA        840

AAATTGAGGT CTGCCACTGT TATTTATGCC AATATAAGCG GCATGTCTG CG
TTTCCCTG        900

GAATATCCCC AAGGTCATAA TGAGAGCCAG AAGATGTGGG TGAGAGATGG AA
CCGTCTGC        960

GGGTCAAATA AGGTTTGCCA GAATCAAAAA TGTGTAGCAG ACACTTTCTT GG
GCTATGAT       1020

TGCAACCTGG AAAAATGCAA CCACCATGGT GTATGTAATA ACAAGAAGAA CT
GCCACTGT       1080

GACCCCACAT ACTTACCTCC AGATTGTAAA AGAATGAAAG ATTCATATCC TG
GCGGGAGC       1140

ATTGATAGTG GCAACAAGGA AAGGGCTGAA CCCATCCCTG TACGGCCCTA CA
TTGCAAGT       1200

CGTTACCGCT CCAAGTCTCC ACGGTGGCCA TTTTTCTTGA TCATCCCTTT CT
ACGTTGTG       1260

ATCCTTGTCC TGATTGGGAT GCTGGTAAAA GTCTATTCCC AAAGGATGAA AT
```

-continued

```
GGAGAATG      1320

GATGACTTCT CAAGCGAAGA GCAATTTGAA AGTGAAAGTG AATCCAAAGA CT
AGTCTGGA      1380

CAGATTCCAC AATGTCACAA GTAATTCTCT TCAGTGGACA GAAAAAAAAG TG
GAAAAGAA      1440

AAGCCTATGC ATTATCTTGC CTGAAAGTCA AGCCTGCATA TCGTGGTCTC CA
TCAGGCCA      1500

GAAATCATAT CTCTCCATTA CACATGTATG ATACATATGT GTGTATATTA TT
CCATAAAT      1560

GATTTACTTG TAAGAAATGA ATGATTATGA ATTTCATATT ATACTTTGAT AT
TTTACCCT      1620

ATTTCTGGTA GTCGGTAGTC ATCAATTGTA TTTTCTAGTA GGTACATTAT AG
AAAAGGCT      1680

ATAAGAAAAT AAATGTGGTA CCATAATAAT CAATATCATA CAACCACCAT CT
AAAAAAGG      1740

TAGGTAGGTA AAAGAATTAT ATTATCAA
              1768
```

(2) INFORMATION FOR SEQ ID NO:4:

(i) SEQUENCE CHARACTERISTICS:
        (A) LENGTH: 457 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Gly Thr Ser Asp Tyr Val Gly Ala Thr Tyr Gln Gly Lys Met Cys Asp
1               5                   10                  15

Lys Asn Tyr Ala Gly Gly Val Ala Leu His Pro Lys Ala Val Thr Leu
            20                  25                  30

Glu Ser Leu Ala Ile Ile Leu Val Gln Leu Leu Ser Leu Ser Met Gly
        35                  40                  45

Leu Ala Tyr Asp Asp Val Asn Lys Cys Gln Cys Gly Val Pro Val Cys
    50                  55                  60

Val Met Asn Pro Glu Ala Pro His Ser Ser Gly Val Arg Ala Phe Ser
65                  70                  75                  80

Asn Cys Ser Met Glu Asp Phe Ser Lys Phe Ile Thr Ser Gln Ser Ser
                85                  90                  95

His Cys Leu Gln Asn Gln Pro Thr Leu Gln Pro Ser Tyr Lys Met Ala
```

-continued

```
                100
                    105
                        110
Val Cys Gly Asn Gly Glu Val Glu Glu Asp Gl
u Ile Cys Asp Cys Gly
        115
            120
                125

Lys Lys Gly Cys Ala Glu Met Pro Pro Pro Cy
s Cys Asn Pro Asp Thr
    130
        135
            140

Cys Lys Leu Ser Asp Gly Ser Glu Cys Ser Se
r Gly Ile Cys Cys Asn
145                 1
50              1
55          1
60

Ser Cys Lys Leu Lys Arg Lys Gly Glu Val Cy
s Arg Leu Ala Gln Asp
            165
                170
                    175

Glu Cys Asp Val Thr Glu Tyr Cys Asn Gly Th
r Ser Glu Val Cys Glu
        180
            185
                190

Asp Phe Phe Val Gln Asn Gly His Pro Cys As
p Asn Arg Lys Trp Ile
    195
        200
            205

Cys Ile Asn Gly Thr Cys Gln Ser Gly Glu Gl
n Gln Cys Gln Asp Leu
    210
        215
            220

Phe Gly Ile Asp Ala Gly Phe Gly Ser Ser Gl
u Cys Phe Trp Glu Leu
225                 2
30              2
35          2
40

Asn Ser Lys Ser Asp Ile Ser Gly Ser Cys Gl
y Ile Ser Ala Gly Gly
            245
                250
                    255

Tyr Lys Glu Cys Pro Pro Asn Asp Arg Met Cy
s Gly Lys Ile Ile Cys
        260
            265
                270

Lys Tyr Gln Ser Glu Asn Ile Leu Lys Leu Ar
g Ser Ala Thr Val Ile
    275
        280
            285

Tyr Ala Asn Ile Ser Gly His Val Cys Val Se
r Leu Glu Tyr Pro Gln
    290
        295
            300

Gly His Asn Glu Ser Gln Lys Met Trp Val Ar
g Asp Gly Thr Val Cys
```

```
305                     3
10                      3
15                      3
20

Gly Ser Asn Lys Val Cys Gln Asn Gln Lys Cy
s Val Ala Asp Thr Phe
              325
                 330
                    335

Leu Gly Tyr Asp Cys Asn Leu Glu Lys Cys As
n His His Gly Val Cys
              340
                 345
                    350

Asn Asn Lys Lys Asn Cys His Cys Asp Pro Th
r Tyr Leu Pro Pro Asp
              355
                 360
                    365

Cys Lys Arg Met Lys Asp Ser Tyr Pro Gly Gl
y Ser Ile Asp Ser Gly
           370
              375
                 380

Asn Lys Glu Arg Ala Glu Pro Ile Pro Val Ar
g Pro Tyr Ile Ala Ser
385                     3
90                      3
95                      4
00

Arg Tyr Arg Ser Lys Ser Pro Arg Trp Pro Ph
e Phe Leu Ile Ile Pro
                 405
                    410
                       415

Phe Tyr Val Val Ile Leu Val Leu Ile Gly Me
t Leu Val Lys Val Tyr
                 420
                    425
                       430

Ser Gln Arg Met Lys Trp Arg Met Asp Asp Ph
e Ser Ser Glu Glu Gln
           435
              440
                 445

Phe Glu Ser Glu Ser Glu Ser Lys Asp
        450
           455

(2) INFORMATION FOR SEQ ID NO:5:

(i) SEQUENCE CHARACTERISTICS:
         (A) LENGTH: 2553 base
pairs
         (B) TYPE: nucleic acid
         (C) STRANDEDNESS: double
         (D) TOPOLOGY: linear (ii) MOLECULE TYPE: cDNA (ix) FEATURE:
         (A) NAME/KEY: CDS
         (B) LOCATION: 17..2221

(xi) SEQUENCE DESCRIPTION: SEQ ID NO:5:

TGAGGAGGAC CAGCGC ATG CGG CTC ATC TTG CTT CTA
CTG AGT GGG CTG            49

Met Arg Leu Ile Leu Leu Leu Ser Gly L
``` eu

```
          1               5
                              10
```

```
AGT GAA CTT GGC GGC CTT AGC CAG TCC CAA AC
A GAA GGC ACT CGT GAG            97
Ser Glu Leu Gly Gly Leu Ser Gln Ser Gln Th
r Glu Gly Thr Arg Glu
                15
                    20
                        25
```

```
AAA TTA CAC GTG CAA GTC ACA GTG CCA GAG AA
A ATC CGG TCC GTC ACA            145
Lys Leu His Val Gln Val Thr Val Pro Glu Ly
s Ile Arg Ser Val Thr
           30
               35
                   40
```

```
AGC AAT GGC TAC GAA ACA CAG GTG ACC TAC AA
T CTC AAA ATC GAA GGG            193
Ser Asn Gly Tyr Glu Thr Gln Val Thr Tyr As
n Leu Lys Ile Glu Gly
         45
             50
                 55
```

```
AAA ACA TAC ACC TTG GAC CTA ATG CAA AAA CC
G TTC TTG CCT CCC AAC            241
Lys Thr Tyr Thr Leu Asp Leu Met Gln Lys Pr
o Phe Leu Pro Pro Asn
 60
 65
 70
 75
```

```
TTT AGA GTA TAC AGT TAT GAC AAC GCA GGA AT
C ATG AGG TCT CTT GAG            289
Phe Arg Val Tyr Ser Tyr Asp Asn Ala Gly Il
e Met Arg Ser Leu Glu
               80
                   85
                       90
```

```
CAG AAG TTT CAG AAT ATC TGC TAC TTC CAA GG
A TAC ATT GAA GGT TAT            337
Gln Lys Phe Gln Asn Ile Cys Tyr Phe Gln Gl
y Tyr Ile Glu Gly Tyr
             95
                100
                   105
```

```
CCA AAT TCT ATG GTG ATT GTT AGC ACA TGT AC
T GGA CTG AGG GGT TTT            385
Pro Asn Ser Met Val Ile Val Ser Thr Cys Th
r Gly Leu Arg Gly Phe
          110
              115
                  120
```

```
CTC CAA TTT GGA AAC GTT AGC TAT GGA ATT GA
A CCT CTG GAA TCT TCC            433
Leu Gln Phe Gly Asn Val Ser Tyr Gly Ile Gl
u Pro Leu Glu Ser Ser
     125
         130
             135
```

```
AGT GGT TTT GAA CAC GTG ATC TAC CAA GTG GA
A CCT GAG AAA GGA GGT            481
Ser Gly Phe Glu His Val Ile Tyr Gln Val Gl
u Pro Glu Lys Gly Gly
140                   1
 45                  1
 50                  1
 55
```

```
GCA TTA CTC TAC GCC GAG AAG GAT ATC GAT TT
```

```
A AGA GAC TCG CAG TAT        529
Ala Leu Leu Tyr Ala Glu Lys Asp Ile Asp Le
u Arg Asp Ser Gln Tyr
           160
               165
                   170

AAG ATA CGA AGT ATC AAG CCA CAG CGG ATC GT
C TCT CAC TAT TTG GAA        577
Lys Ile Arg Ser Ile Lys Pro Gln Arg Ile Va
l Ser His Tyr Leu Glu
       175
           180
               185

ATA CAT ATT GTC GTT GAA AAG CAA ATG TTT GA
G CAT ATC GGG GCT GAT        625
Ile His Ile Val Val Glu Lys Gln Met Phe Gl
u His Ile Gly Ala Asp
      190
          195
              200

ACA GCC ATT GTC ACT CAA AAG ATT TTC CAG TT
G ATT GGA CTG GCA AAT        673
Thr Ala Ile Val Thr Gln Lys Ile Phe Gln Le
u Ile Gly Leu Ala Asn
      205
          210
              215

GCT ATC TTT GCC CCC TTT AAT CTT ACA GTA AT
T CTG TCT TCC CTG GAA        721
Ala Ile Phe Ala Pro Phe Asn Leu Thr Val Il
e Leu Ser Ser Leu Glu
220                 2
25                    2
30                      2
35

TTT TGG ATG GAT GAA AAC AAA ATC TTG ACC AC
A GGC GAT GCT AAC AAG        769
Phe Trp Met Asp Glu Asn Lys Ile Leu Thr Th
r Gly Asp Ala Asn Lys
        240
            245
                250

TTG CTC TAC AGG TTC CTG AAG TGG AAA CAG TC
G TAC CTT GTT CTG CGA        817
Leu Leu Tyr Arg Phe Leu Lys Trp Lys Gln Se
r Tyr Leu Val Leu Arg
       255
           260
               265

CCA CAT GAT ATG GCG TTT TTA CTC GTC TAC AG
G AAC ACT ACC GAT TAT        865
Pro His Asp Met Ala Phe Leu Leu Val Tyr Ar
g Asn Thr Thr Asp Tyr
        270
            275
                280

GTT GGC GCT ACC TAT CAA GGG AAG ATG TGT GA
C AAG AAC TAT GCA GGA        913
Val Gly Ala Thr Tyr Gln Gly Lys Met Cys As
p Lys Asn Tyr Ala Gly
      285
          290
              295

GGA GTT GCT TTG CAC CCC AAA GCC GTA ACT CT
G GAA TCA CTT GCA ATT        961
Gly Val Ala Leu His Pro Lys Ala Val Thr Le
u Glu Ser Leu Ala Ile
300                 3
05                    3
10                      3
15
```

```
ATT TTA GTT CAG CTG CTG AGC CTC AGC ATG GG
G CTA GCG TAT GAC GAC           1009
Ile Leu Val Gln Leu Leu Ser Leu Ser Met Gl
y Leu Ala Tyr Asp Asp
            320
                325
                    330

GTG AAC AAG TGC CAG TGT GGC GTA CCT GTC TG
C GTG ATG AAC CCG GAA           1057
Val Asn Lys Cys Gln Cys Gly Val Pro Val Cy
s Val Met Asn Pro Glu
        335
            340
                345

GCG CCT CAC TCC AGC GGT GTC CGG GCC TTC AG
T AAC TGC AGC ATG GAG           1105
Ala Pro His Ser Ser Gly Val Arg Ala Phe Se
r Asn Cys Ser Met Glu
        350
            355
                360

GAC TTT TCC AAG TTT ATC ACA AGT CAA AGC TC
C CAC TGT CTG CAG AAC           1153
Asp Phe Ser Lys Phe Ile Thr Ser Gln Ser Se
r His Cys Leu Gln Asn
      365
        370
            375

CAG CCA ACG CTA CAG CCA TCT TAC AAG ATG GC
G GTC TGT GGG AAT GGA           1201
Gln Pro Thr Leu Gln Pro Ser Tyr Lys Met Al
a Val Cys Gly Asn Gly
380                         3
85                        3
90                      3
95

GAG GTG GAA GAA GAT GAA ATT TGC GAC TGT GG
A AAG AAG GGC TGT GCA           1249
Glu Val Glu Glu Asp Glu Ile Cys Asp Cys Gl
y Lys Lys Gly Cys Ala
                400
                    405
                        410

GAA ATG CCC CCG CCA TGC TGT AAC CCC GAC AC
C TGT AAG CTG TCA GAT           1297
Glu Met Pro Pro Pro Cys Cys Asn Pro Asp Th
r Cys Lys Leu Ser Asp
            415
                420
                    425

GGC TCC GAG TGC TCC AGC GGG ATA TGC TGC AA
C TCG TGC AAG CTG AAG           1345
Gly Ser Glu Cys Ser Ser Gly Ile Cys Cys As
n Ser Cys Lys Leu Lys
        430
            435
                440

CGG AAA GGG GAG GTT TGC AGG CTT GCC CAA GA
T GAG TGT GAT GTC ACA           1393
Arg Lys Gly Glu Val Cys Arg Leu Ala Gln As
p Glu Cys Asp Val Thr
        445
            450
                455

GAG TAC TGC AAC GGC ACA TCC GAA GTG TGT GA
A GAC TTC TTT GTT CAA           1441
Glu Tyr Cys Asn Gly Thr Ser Glu Val Cys Gl
u Asp Phe Phe Val Gln
460                         4
65                      4
```

```
  70                         4
  75

AAC GGT CAC CCA TGT GAC AAT CGC AAG TGG AT
C TGT ATT AAC GGC ACC                   1489
Asn Gly His Pro Cys Asp Asn Arg Lys Trp Il
e Cys Ile Asn Gly Thr
            480
                  485
                        490

TGT CAG AGT GGA GAA CAG CAG TGC CAG GAT CT
A TTT GGC ATC GAT GCA                   1537
Cys Gln Ser Gly Glu Gln Gln Cys Gln Asp Le
u Phe Gly Ile Asp Ala
              495
                    500
                          505

GGC TTT GGT TCA AGT GAA TGT TTC TGG GAG CT
G AAT TCC AAG AGC GAC                   1585
Gly Phe Gly Ser Ser Glu Cys Phe Trp Glu Le
u Asn Ser Lys Ser Asp
          510
                515
                      520

ATA TCT GGG AGC TGT GGA ATC TCT GCT GGG GG
A TAC AAG GAA TGC CCA                   1633
Ile Ser Gly Ser Cys Gly Ile Ser Ala Gly Gl
y Tyr Lys Glu Cys Pro
        525
              530
                    535

CCT AAT GAC CGG ATG TGT GGG AAA ATA ATA TG
T AAA TAC CAA AGT GAA                   1681
Pro Asn Asp Arg Met Cys Gly Lys Ile Ile Cy
s Lys Tyr Gln Ser Glu
540                       5
  45                        5
    50                        5
      55

AAT ATA CTA AAA TTG AGG TCT GCC ACT GTT AT
T TAT GCC AAT ATA AGC                   1729
Asn Ile Leu Lys Leu Arg Ser Ala Thr Val Il
e Tyr Ala Asn Ile Ser
                560
                      565
                            570

GGG CAT GTC TGC GTT TCC CTG GAA TAT CCC CA
A GGT CAT AAT GAG AGC                   1777
Gly His Val Cys Val Ser Leu Glu Tyr Pro Gl
n Gly His Asn Glu Ser
            575
                  580
                        585

CAG AAG ATG TGG GTG AGA GAT GGA ACC GTC TG
C GGG TCA AAT AAG GTT                   1825
Gln Lys Met Trp Val Arg Asp Gly Thr Val Cy
s Gly Ser Asn Lys Val
        590
              595
                    600

TGC CAG AAT CAA AAA TGT GTA GCA GAC ACT TT
C TTG GGC TAT GAT TGC                   1873
Cys Gln Asn Gln Lys Cys Val Ala Asp Thr Ph
e Leu Gly Tyr Asp Cys
          605
                610
                      615

AAC CTG GAA AAA TGC AAC CAC CAT GGT GTA TG
T AAT AAC AAG AAG AAC                   1921
Asn Leu Glu Lys Cys Asn His His Gly Val Cy
s Asn Asn Lys Lys Asn
```

```
620             6
  25            6
  30            6
  35

TGC CAC TGT GAC CCC ACA TAC TTA CCT CCA GA
T TGT AAA AGA ATG AAA           1969
Cys His Cys Asp Pro Thr Tyr Leu Pro Pro As
p Cys Lys Arg Met Lys
             640
               645
                 650

GAT TCA TAT CCT GGC GGG AGC ATT GAT AGT GG
C AAC AAG GAA AGG GCT           2017
Asp Ser Tyr Pro Gly Gly Ser Ile Asp Ser Gl
y Asn Lys Glu Arg Ala
             655
               660
                 665

GAA CCC ATC CCT GTA CGG CCC TAC ATT GCA AG
T CGT TAC CGC TCC AAG           2065
Glu Pro Ile Pro Val Arg Pro Tyr Ile Ala Se
r Arg Tyr Arg Ser Lys
           670
             675
               680

TCT CCA CGG TGG CCA TTT TTC TTG ATC ATC CC
T TTC TAC GTT GTG ATC           2113
Ser Pro Arg Trp Pro Phe Phe Leu Ile Ile Pr
o Phe Tyr Val Val Ile
      685
        690
          695

CTT GTC CTG ATT GGG ATG CTG GTA AAA GTC TA
T TCC CAA AGG ATG AAA           2161
Leu Val Leu Ile Gly Met Leu Val Lys Val Ty
r Ser Gln Arg Met Lys
700                    7
  05                 7
    10             7
      15

TGG AGA ATG GAT GAC TTC TCA AGC GAA GAG CA
A TTT GAA AGT GAA AGT           2209
Trp Arg Met Asp Asp Phe Ser Ser Glu Glu Gl
n Phe Glu Ser Glu Ser
                 720
                   725
                     730

GAA TCC AAA GAC TAGTCTGGAC AGATTCCACA ATGTCACAAG TA
ATTCTCTT        2261
Glu Ser Lys Asp
          735

CAGTGGACAG AAAAAAAAGT GGAAAAGAAA AGCCTATGCA TTATCTTGCC TG
AAAGTCAA       2321

GCCTGCATAT CGTGGTCTCC ATCAGGCCAG AAATCATATC TCTCCATTAC AC
ATGTATGA       2381

TACATATGTG TGTATATTAT TCCATAAATG ATTTACTTGT AAGAAATGAA TG
ATTATGAA       2441

TTTCATATTA TACTTTGATA TTTTACCCTA TTTCTGGTAG TCGGTAGTCA TC
AATTGTAT       2501

TTTCTAGTAG GTACATTATA GAAAAGGCTA TAAGAAAATA AATGTGGTAC CA
          2553

(2) INFORMATION FOR SEQ ID NO:6:

(i) SEQUENCE CHARACTERISTICS:
        (A) LENGTH: 735 amino
acids
```

(B) TYPE: amino acid
(D) TOPOLOGY: linear (ii) MOLECULE TYPE: protein (xi) SEQUENCE DESCRIPTION: SEQ ID NO:6:

Met Arg Leu Ile Leu Leu Leu Ser Gly Leu Ser Glu Leu Gly Gly
1               5                  10                  15

Leu Ser Gln Ser Gln Thr Glu Gly Thr Arg Glu Lys Leu His Val Gln
            20                  25                  30

Val Thr Val Pro Glu Lys Ile Arg Ser Val Thr Ser Asn Gly Tyr Glu
        35                  40                  45

Thr Gln Val Thr Tyr Asn Leu Lys Ile Glu Gly Lys Thr Tyr Thr Leu
    50                  55                  60

Asp Leu Met Gln Lys Pro Phe Leu Pro Pro Asn Phe Arg Val Tyr Ser
65                  70                  75                  80

Tyr Asp Asn Ala Gly Ile Met Arg Ser Leu Glu Gln Lys Phe Gln Asn
                85                  90                  95

Ile Cys Tyr Phe Gln Gly Tyr Ile Glu Gly Tyr Pro Asn Ser Met Val
            100                 105                 110

Ile Val Ser Thr Cys Thr Gly Leu Arg Gly Phe Leu Gln Phe Gly Asn
        115                 120                 125

Val Ser Tyr Gly Ile Glu Pro Leu Glu Ser Ser Ser Gly Phe Glu His
    130                 135                 140

Val Ile Tyr Gln Val Glu Pro Glu Lys Gly Ala Leu Leu Tyr Ala
145                 150                 155                 160

Glu Lys Asp Ile Asp Leu Arg Asp Ser Gln Tyr Lys Ile Arg Ser Ile
                165                 170                 175

Lys Pro Gln Arg Ile Val Ser His Tyr Leu Glu Ile His Ile Val Val
            180                 185                 190

Glu Lys Gln Met Phe Glu His Ile Gly Ala Asp Thr Ala Ile Val Thr
195 200 205

Gln Lys Ile Phe Gln Leu Ile Gly Leu Ala Asn Ala Ile Phe Ala Pro
210 215 220

Phe Asn Leu Thr Val Ile Leu Ser Ser Leu Glu Phe Trp Met Asp Glu
225 230 235 240

Asn Lys Ile Leu Thr Thr Gly Asp Ala Asn Lys Leu Leu Tyr Arg Phe
245 250 255

Leu Lys Trp Lys Gln Ser Tyr Leu Val Leu Arg Pro His Asp Met Ala
260 265 270

Phe Leu Leu Val Tyr Arg Asn Thr Thr Asp Tyr Val Gly Ala Thr Tyr
275 280 285

Gln Gly Lys Met Cys Asp Lys Asn Tyr Ala Gly Gly Val Ala Leu His
290 295 300

Pro Lys Ala Val Thr Leu Glu Ser Leu Ala Ile Ile Leu Val Gln Leu
305 310 315 320

Leu Ser Leu Ser Met Gly Leu Ala Tyr Asp Val Asn Lys Cys Gln
325 330 335

Cys Gly Val Pro Val Cys Val Met Asn Pro Glu Ala Pro His Ser Ser
340 345 350

Gly Val Arg Ala Phe Ser Asn Cys Ser Met Glu Asp Phe Ser Lys Phe
355 360 365

Ile Thr Ser Gln Ser Ser His Cys Leu Gln Asn Gln Pro Thr Leu Gln
370 375 380

Pro Ser Tyr Lys Met Ala Val Cys Gly Asn Gly Glu Val Glu Glu Asp
385 390 395 400

```
Glu Ile Cys Asp Cys Gly Lys Lys Gly Cys Al
a Glu Met Pro Pro Pro
            405
            410
            415

Cys Cys Asn Pro Asp Thr Cys Lys Leu Ser As
p Gly Ser Glu Cys Ser
            420
            425
            430

Ser Gly Ile Cys Cys Asn Ser Cys Lys Leu Ly
s Arg Lys Gly Glu Val
            435
            440
            445

Cys Arg Leu Ala Gln Asp Glu Cys Asp Val Th
r Glu Tyr Cys Asn Gly
        450
        455
        460

Thr Ser Glu Val Cys Glu Asp Phe Phe Val Gl
n Asn Gly His Pro Cys
465                 4
70                  4
75                  4
80

Asp Asn Arg Lys Trp Ile Cys Ile Asn Gly Th
r Cys Gln Ser Gly Glu
            485
            490
            495

Gln Gln Cys Gln Asp Leu Phe Gly Ile Asp Al
a Gly Phe Gly Ser Ser
            500
            505
            510

Glu Cys Phe Trp Glu Leu Asn Ser Lys Ser As
p Ile Ser Gly Ser Cys
        515
        520
        525

Gly Ile Ser Ala Gly Gly Tyr Lys Glu Cys Pr
o Pro Asn Asp Arg Met
        530
        535
        540

Cys Gly Lys Ile Ile Cys Lys Tyr Gln Ser Gl
u Asn Ile Leu Lys Leu
545                 5
50                  5
55                  5
60

Arg Ser Ala Thr Val Ile Tyr Ala Asn Ile Se
r Gly His Val Cys Val
            565
            570
            575

Ser Leu Glu Tyr Pro Gln Gly His Asn Glu Se
r Gln Lys Met Trp Val
            580
            585
            590

Arg Asp Gly Thr Val Cys Gly Ser Asn Lys Va
l Cys Gln Asn Gln Lys
        595
        600
```

```
                           605
Cys Val Ala Asp Thr Phe Leu Gly Tyr Asp Cy
s Asn Leu Glu Lys Cys
    610
    615
    620

Asn His His Gly Val Cys Asn Asn Lys Lys As
n Cys His Cys Asp Pro
625                 6
30                     6
35                        6
40

Thr Tyr Leu Pro Pro Asp Cys Lys Arg Met Ly
s Asp Ser Tyr Pro Gly
            645
               650
                  655

Gly Ser Ile Asp Ser Gly Asn Lys Glu Arg Al
a Glu Pro Ile Pro Val
            660
               665
                  670

Arg Pro Tyr Ile Ala Ser Arg Tyr Arg Ser Ly
s Ser Pro Arg Trp Pro
        675
           680
              685

Phe Phe Leu Ile Ile Pro Phe Tyr Val Val Il
e Leu Val Leu Ile Gly
    690
    695
    700

Met Leu Val Lys Val Tyr Ser Gln Arg Met Ly
s Trp Arg Met Asp Asp
705                 7
10                     7
15                        7
20

Phe Ser Ser Glu Glu Gln Phe Glu Ser Glu Se
r Glu Ser Lys Asp
                725
                   730
                      735

(2) INFORMATION FOR SEQ ID NO:7:

(i) SEQUENCE CHARACTERISTICS:
        (A) LENGTH: 2650 base
pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 72..2273

(xi) SEQUENCE DESCRIPTION: SEQ ID NO:7:

CATCTCGCAC TTCCAACTGC CCTGTAACCA CCAACTGCCC TTATTCCGGC TG
GGACCCAG         60

GACTTCAAGC C ATG TGG GTC TTG TTT CTG CTC AGC
GGG CTC GGC GGG CTG         110
            Met Trp Val
Leu Phe Leu Leu Ser Gly Leu Gly Gly Leu 740
           745
```

-continued

```
CGG ATG GAC AGT AAT TTT GAT AGT TTA CCT GT
G CAA ATT ACA GTT CCG           158
Arg Met Asp Ser Asn Phe Asp Ser Leu Pro Va
l Gln Ile Thr Val Pro
     750
         755
             760

GAG AAA ATA CGG TCA ATA ATA AAG GAA GGA AT
T GAA TCG CAG GCA TCC           206
Glu Lys Ile Arg Ser Ile Ile Lys Glu Gly Il
e Glu Ser Gln Ala Ser
765             7
70              7
75              7
80

TAC AAA ATT GTA ATT GAA GGG AAA CCA TAT AC
T GTG AAT TTA ATG CAA           254
Tyr Lys Ile Val Ile Glu Gly Lys Pro Tyr Th
r Val Asn Leu Met Gln
         785
             790
                 795

AAA AAC TTT TTA CCC CAT AAT TTT AGA GTT TA
C AGT TAT AGT GGC ACA           302
Lys Asn Phe Leu Pro His Asn Phe Arg Val Ty
r Ser Tyr Ser Gly Thr
         800
             805
                 810

GGA ATT ATG AAA CCA CTT GAC CAA GAT TTT CA
G AAT TTC TGC CAC TAC           350
Gly Ile Met Lys Pro Leu Asp Gln Asp Phe Gl
n Asn Phe Cys His Tyr
         815
             820
                 825

CAA GGG TAT ATT GAA GGT TAT CCA AAA TCT GT
G GTG ATG GTT AGC ACA           398
Gln Gly Tyr Ile Glu Gly Tyr Pro Lys Ser Va
l Val Met Val Ser Thr
     830
         835
             840

TGT ACT GGA CTC AGG GGC GTA CTA CAG TTT GA
A AAT GTT AGT TAT GGA           446
Cys Thr Gly Leu Arg Gly Val Leu Gln Phe Gl
u Asn Val Ser Tyr Gly
845             8
50              8
55              8
60

ATA GAA CCC CTG GAG TCT TCA GTT GGC TTT GA
A CAT GTA ATT TAC CAA           494
Ile Glu Pro Leu Glu Ser Ser Val Gly Phe Gl
u His Val Ile Tyr Gln
             865
                 870
                     875

GTA AAA CAT AAG AAA GCA GAT GTT TCC TTA TA
T AAT GAG AAG GAT ATT           542
Val Lys His Lys Lys Ala Asp Val Ser Leu Ty
r Asn Glu Lys Asp Ile
             880
                 885
                     890

GAA TCA AGA GAT CTG TCC TTT AAA TTA CAA AG
C GCA GAG CCA CAG CAA           590
Glu Ser Arg Asp Leu Ser Phe Lys Leu Gln Se
r Ala Glu Pro Gln Gln
         895
```

```
                                900
                                905

GAT TTT GCA AAG TAT ATA GAA ATG CAT GTT AT
A GTT GAA AAA CAA TTG           638
Asp Phe Ala Lys Tyr Ile Glu Met His Val Il
e Val Glu Lys Gln Leu
     910
       915
         920

TAT AAT CAT ATG GGG TCT GAT ACA ACT GTT GT
C GCT CAA AAA GTT TTC           686
Tyr Asn His Met Gly Ser Asp Thr Thr Val Va
l Ala Gln Lys Val Phe
925                 9
30                    9
  35                    9
    40

CAG TTG ATT GGA TTG ACG AAT GCT ATT TTT GT
T TCA TTT AAT ATT ACA           734
Gln Leu Ile Gly Leu Thr Asn Ala Ile Phe Va
l Ser Phe Asn Ile Thr
         945
           950
             955

ATT ATT CTG TCT TCA TTG GAG CTT TGG ATA GA
T GAA AAT AAA ATT GCA           782
Ile Ile Leu Ser Ser Leu Glu Leu Trp Ile As
p Glu Asn Lys Ile Ala
             960
               965
                 970

ACC ACT GGA GAA GCT AAT GAG TTA TTA CAC AC
A TTT TTA AGA TGG AAA           830
Thr Thr Gly Glu Ala Asn Glu Leu Leu His Th
r Phe Leu Arg Trp Lys
                 975
                   980
                     985

ACA TCT TAT CTT GTT TTA CGT CCT CAT GAT GT
G GCA TTT TTA CTT GTT           878
Thr Ser Tyr Leu Val Leu Arg Pro His Asp Va
l Ala Phe Leu Leu Val
         990
           995
             1000

TAC AGA GAA AAG TCA AAT TAT GTT GGT GCA AC
C TTT CAA GGG AAG ATG           926
Tyr Arg Glu Lys Ser Asn Tyr Val Gly Ala Th
r Phe Gln Gly Lys Met
1005                1010
              1015
                1020

TGT GAT GCA AAC TAT GCA GGA GGT GTT GTT CT
G CAC CCC AGA ACC ATA           974
Cys Asp Ala Asn Tyr Ala Gly Gly Val Val Le
u His Pro Arg Thr Ile
              1025
                1030
                  1035

AGT CTG GAA TCA CTT GCA GTT ATT TTA GCT CA
A TTA TTG AGC CTT AGT           1022
Ser Leu Glu Ser Leu Ala Val Ile Leu Ala Gl
n Leu Leu Ser Leu Ser
                  1040
                    1045
                      1050

ATG GGG ATC ACT TAT GAT GAC ATT AAC AAA TG
C CAG TGC TCA GGA GCT           1070
Met Gly Ile Thr Tyr Asp Asp Ile Asn Lys Cy
s Gln Cys Ser Gly Ala
```

```
                              1055
                                   1060
                                        1065

GTC TGC ATT ATG AAT CCA GAA GCA ATT CAT TT
C AGT GGT GTG AAG ATC       1118
Val Cys Ile Met Asn Pro Glu Ala Ile His Ph
e Ser Gly Val Lys Ile
    1070
         1075
              1080

TTT AGT AAC TGC AGC TTC GAA GAC TTT GCA CA
T TTT ATT TCA AAG CAG       1166
Phe Ser Asn Cys Ser Phe Glu Asp Phe Ala Hi
s Phe Ile Ser Lys Gln
1085              1090
         1095
              1100

AAG TCC CAG TGT CTT CAC AAT CAG CCT CGC TT
A GAT CCT TTT TTC AAA       1214
Lys Ser Gln Cys Leu His Asn Gln Pro Arg Le
u Asp Pro Phe Phe Lys
              1105
                   1110
                        1115

CAG CAA GCA GTG TGT GGT AAT GCA AAG CTG GA
A GCA GGA GAG GAG TGT       1262
Gln Gln Ala Val Cys Gly Asn Ala Lys Leu Gl
u Ala Gly Glu Glu Cys
                   1120
                        1125
                             1130

GAC TGT GGG ACT GAA CAG GAT TGT GCC CTT AT
T GGA GAA ACA TGC TGT       1310
Asp Cys Gly Thr Glu Gln Asp Cys Ala Leu Il
e Gly Glu Thr Cys Cys
              1135
                   1140
                        1145

GAT ATT GCC ACA TGT AGA TTT AAA GCC GGT TC
A AAC TGT GCT GAA GGA       1358
Asp Ile Ala Thr Cys Arg Phe Lys Ala Gly Se
r Asn Cys Ala Glu Gly
         1150
              1155
         1160

CCA TGC TGC GAA AAC TGT CTA TTT ATG TCA AA
A GAA AGA ATG TGT AGG       1406
Pro Cys Cys Glu Asn Cys Leu Phe Met Ser Ly
s Glu Arg Met Cys Arg
1165                   1170
                   1175
                        1180

CCT TCC TTT GAA GAA TGC GAC CTC CCT GAA TA
T TGC AAT GGA TCA TCT       1454
Pro Ser Phe Glu Glu Cys Asp Leu Pro Glu Ty
r Cys Asn Gly Ser Ser
                   1185
                        1190
                             1195

GCA TCA TGC CCA GAA AAC CAC TAT GTT CAG AC
T GGG CAT CCG TGT GGA       1502
Ala Ser Cys Pro Glu Asn His Tyr Val Gln Th
r Gly His Pro Cys Gly
                        1200
                             1205
                                  1210

CTG AAT CAA TGG ATC TGT ATA GAT GGA GTT TG
T ATG AGT GGG GAT AAA       1550
Leu Asn Gln Trp Ile Cys Ile Asp Gly Val Cy
s Met Ser Gly Asp Lys
```

-continued

```
          1215
          1220
          1225

CAA TGT ACA GAC ACA TTT GGC AAA GAA GTA GA
G TTT GGC CCT TCA GAA          1598
Gln Cys Thr Asp Thr Phe Gly Lys Glu Val Gl
u Phe Gly Pro Ser Glu
     1230
          1235
               1240

TGT TAT TCT CAC CTT AAT TCA AAG ACT GAT GT
A TCT GGA AAC TGT GGT          1646
Cys Tyr Ser His Leu Asn Ser Lys Thr Asp Va
l Ser Gly Asn Cys Gly
1245                1250
          1255
               1260

ATA AGT GAT TCA GGA TAC ACA CAG TGT GAA GC
T GAC AAT CTG CAG TGC          1694
Ile Ser Asp Ser Gly Tyr Thr Gln Cys Glu Al
a Asp Asn Leu Gln Cys
          1265
               1270
                    1275

GGA AAA TTA ATA TGT AAA TAT GTA GGT AAA TT
T TTA TTA CAA ATT CCA          1742
Gly Lys Leu Ile Cys Lys Tyr Val Gly Lys Ph
e Leu Leu Gln Ile Pro
          1280
               1285
                    1290

AGA GCC ACT ATT ATT TAT GCC AAC ATA AGT GG
A CAT CTC TGC ATT GCT          1790
Arg Ala Thr Ile Ile Tyr Ala Asn Ile Ser Gl
y His Leu Cys Ile Ala
          1295
               1300
                    1305

GTG GAA TTT GCC AGT GAT CAT GCA GAC AGC CA
A AAG ATG TGG ATA AAA          1838
Val Glu Phe Ala Ser Asp His Ala Asp Ser Gl
n Lys Met Trp Ile Lys
     1310
          1315
               1320

GAT GGA ACT TCT TGT GGT TCA AAT AAG GTT TG
C AGG AAT CAA AGA TGT          1886
Asp Gly Thr Ser Cys Gly Ser Asn Lys Val Cy
s Arg Asn Gln Arg Cys
1325                1330
          1335
               1340

GTG AGT TCT TCA TAC TTG GGT TAT GAT TGT AC
T ACT GAC AAA TGC AAT          1934
Val Ser Ser Ser Tyr Leu Gly Tyr Asp Cys Th
r Thr Asp Lys Cys Asn
          1345
               1350
                    1355

GAT AGA GGT GTA TGC AAT AAC AAA AAG CAC TG
T CAC TGT AGT GCT TCA          1982
Asp Arg Gly Val Cys Asn Asn Lys Lys His Cy
s His Cys Ser Ala Ser
          1360
               1365
                    1370

TAT TTA CCT CCA GAT TGC TCA GTT CAA TCA GA
T CTA TGG CCT GGT GGG          2030
Tyr Leu Pro Pro Asp Cys Ser Val Gln Ser As
p Leu Trp Pro Gly Gly
```

```
              1375
              1380
              1385

AGT ATT GAC AGT GGC AAT TTT CCA CCT GTA GC
T ATA CCA GCC AGA CTC          2078
Ser Ile Asp Ser Gly Asn Phe Pro Pro Val Al
a Ile Pro Ala Arg Leu
      1390
              1395
                      1400

CCT GAA AGG CGC TAC ATT GAG AAC ATT TAC CA
T TCC AAA CCA ATG AGA          2126
Pro Glu Arg Arg Tyr Ile Glu Asn Ile Tyr Hi
s Ser Lys Pro Met Arg
 1405                  1410
              1415
                      1420

TGG CCA TTT TTC TTA TTC ATT CCT TTC TTT AT
T ATT TTC TGT GTA CTG          2174
Trp Pro Phe Phe Leu Phe Ile Pro Phe Phe Il
e Ile Phe Cys Val Leu
                  1425
              1430
                      1435

ATT GCT ATA ATG GTG AAA GTT AAT TTC CAA AG
G AAA AAA TGG AGA ACT          2222
Ile Ala Ile Met Val Lys Val Asn Phe Gln Ar
g Lys Lys Trp Arg Thr
              1440
              1445
                      1450

GAG GAC TAT TCA AGC GAT GAG CAA CCT GAA AG
T GAG AGT GAA CCT AAA          2270
Glu Asp Tyr Ser Ser Asp Glu Gln Pro Glu Se
r Glu Ser Glu Pro Lys
              1455
              1460
                      1465

GGG TAGTCTGGAC AACAGAGATG CCATGATATC ACTTCTTCTA GAGTAATTA
T         2323
Gly

CTGTGATGGA TGGACACAAA AAAATGGAAA GAAAAGAATG TACATTACCT GG
TTTCCTGG       2383

GATTCAAACC TGCATATTGT GATTTTAATT TGACCAGAAA ATATGATATA TA
TGTATAAT       2443

TTCACAGATA ATTTACTTAT TTAAAAATGC ATGATAATGA GTTTTACATT AC
AAATTTCT       2503

GTTTTTTTAA AGTTATCTTA CGCTATTTCT GTTGGTTAGT AGACACTAAT TC
TGTCAGTA       2563

GGGGCATGGT ATAAGGAAAT ATCATAATGT AATGAGGTGG TACTATGATT AA
AAGCCACT       2623

GTTACATTTC AAAAAAAAAA AAAAAAA
         2650

(2) INFORMATION FOR SEQ ID NO:8:

(i) SEQUENCE CHARACTERISTICS:
        (A) LENGTH: 734 amino
acids
        (B) TYPE: amino acid
        (D) TOPOLOGY: linear (ii) MOLECULE TYPE: protein (xi) SEQUENCE DESCRIPTION: SEQ ID NO:8:
```

Met Trp Val Leu Phe Leu Leu Ser Gly Leu Gl
y Gly Leu Arg Met Asp
 1               5
                    10
                        15

Ser Asn Phe Asp Ser Leu Pro Val Gln Ile Th
r Val Pro Glu Lys Ile
         20
             25
                 30

Arg Ser Ile Ile Lys Glu Gly Ile Glu Ser Gl
n Ala Ser Tyr Lys Ile
         35
             40
                 45

Val Ile Glu Gly Lys Pro Tyr Thr Val Asn Le
u Met Gln Lys Asn Phe
     50
         55
             60

Leu Pro His Asn Phe Arg Val Tyr Ser Tyr Se
r Gly Thr Gly Ile Met
 65
     70
         75
             80

Lys Pro Leu Asp Gln Asp Phe Gln Asn Phe Cy
s His Tyr Gln Gly Tyr
                 85
                     90
                         95

Ile Glu Gly Tyr Pro Lys Ser Val Val Met Va
l Ser Thr Cys Thr Gly
             100
                 105
                     110

Leu Arg Gly Val Leu Gln Phe Glu Asn Val Se
r Tyr Gly Ile Glu Pro
         115
             120
                 125

Leu Glu Ser Ser Val Gly Phe Glu His Val Il
e Tyr Gln Val Lys His
     130
         135
             140

Lys Lys Ala Asp Val Ser Leu Tyr Asn Glu Ly
s Asp Ile Glu Ser Arg
145               1
50                1
55                1
60

Asp Leu Ser Phe Lys Leu Gln Ser Ala Glu Pr
o Gln Gln Asp Phe Ala
             165
                 170
                     175

Lys Tyr Ile Glu Met His Val Ile Val Glu Ly
s Gln Leu Tyr Asn His
         180
             185
                 190

Met Gly Ser Asp Thr Thr Val Val Ala Gln Ly
s Val Phe Gln Leu Ile
     195
         200
             205

```
Gly Leu Thr Asn Ala Ile Phe Val Ser Phe As
n Ile Thr Ile Ile Leu
    210
        215
            220

Ser Ser Leu Glu Leu Trp Ile Asp Glu Asn Ly
s Ile Ala Thr Thr Gly
225                 2
30                    2
35                      2
40

Glu Ala Asn Glu Leu Leu His Thr Phe Leu Ar
g Trp Lys Thr Ser Tyr
        245
            250
                255

Leu Val Leu Arg Pro His Asp Val Ala Phe Le
u Leu Val Tyr Arg Glu
            260
                265
                    270

Lys Ser Asn Tyr Val Gly Ala Thr Phe Gln Gl
y Lys Met Cys Asp Ala
        275
            280
                285

Asn Tyr Ala Gly Gly Val Val Leu His Pro Ar
g Thr Ile Ser Leu Glu
    290
        295
            300

Ser Leu Ala Val Ile Leu Ala Gln Leu Leu Se
r Leu Ser Met Gly Ile
305                 3
10                    3
15                      3
20

Thr Tyr Asp Asp Ile Asn Lys Cys Gln Cys Se
r Gly Ala Val Cys Ile
                325
                    330
                        335

Met Asn Pro Glu Ala Ile His Phe Ser Gly Va
l Lys Ile Phe Ser Asn
            340
                345
                    350

Cys Ser Phe Glu Asp Phe Ala His Phe Ile Se
r Lys Gln Lys Ser Gln
        355
            360
                365

Cys Leu His Asn Gln Pro Arg Leu Asp Pro Ph
e Phe Lys Gln Gln Ala
    370
        375
            380

Val Cys Gly Asn Ala Lys Leu Glu Ala Gly Gl
u Glu Cys Asp Cys Gly
385                 3
90                    3
95                      4
00

Thr Glu Gln Asp Cys Ala Leu Ile Gly Glu Th
r Cys Cys Asp Ile Ala
                405
                    410
                        415
```

```
Thr Cys Arg Phe Lys Ala Gly Ser Asn Cys Al
a Glu Gly Pro Cys Cys
        420
            425
                430

Glu Asn Cys Leu Phe Met Ser Lys Glu Arg Me
t Cys Arg Pro Ser Phe
        435
            440
                445

Glu Glu Cys Asp Leu Pro Glu Tyr Cys Asn Gl
y Ser Ser Ala Ser Cys
        450
    455
        460

Pro Glu Asn His Tyr Val Gln Thr Gly His Pr
o Cys Gly Leu Asn Gln
465                 4
70              4
75          4
80

Trp Ile Cys Ile Asp Gly Val Cys Met Ser Gl
y Asp Lys Gln Cys Thr
        485
            490
                495

Asp Thr Phe Gly Lys Glu Val Glu Phe Gly Pr
o Ser Glu Cys Tyr Ser
        500
            505
                510

His Leu Asn Ser Lys Thr Asp Val Ser Gly As
n Cys Gly Ile Ser Asp
        515
            520
                525

Ser Gly Tyr Thr Gln Cys Glu Ala Asp Asn Le
u Gln Cys Gly Lys Leu
        530
    535
        540

Ile Cys Lys Tyr Val Gly Lys Phe Leu Leu Gl
n Ile Pro Arg Ala Thr
545                 5
50              5
55          5
60

Ile Ile Tyr Ala Asn Ile Ser Gly His Leu Cy
s Ile Ala Val Glu Phe
            565
                570
                    575

Ala Ser Asp His Ala Asp Ser Gln Lys Met Tr
p Ile Lys Asp Gly Thr
            580
                585
                    590

Ser Cys Gly Ser Asn Lys Val Cys Arg Asn Gl
n Arg Cys Val Ser Ser
        595
            600
                605

Ser Tyr Leu Gly Tyr Asp Cys Thr Thr Asp Ly
s Cys Asn Asp Arg Gly
    610
        615
            620
```

-continued

```
Val Cys Asn Asn Lys Lys His Cys His Cys Se
r Ala Ser Tyr Leu Pro
625                                           6
30                                            6
35                                            6
40

Pro Asp Cys Ser Val Gln Ser Asp Leu Trp Pr
o Gly Gly Ser Ile Asp
                645
                650
                655

Ser Gly Asn Phe Pro Pro Val Ala Ile Pro Al
a Arg Leu Pro Glu Arg
            660
            665
            670

Arg Tyr Ile Glu Asn Ile Tyr His Ser Lys Pr
o Met Arg Trp Pro Phe
        675
        680
        685

Phe Leu Phe Ile Pro Phe Phe Ile Ile Phe Cy
s Val Leu Ile Ala Ile
    690
    695
    700

Met Val Lys Val Asn Phe Gln Arg Lys Lys Tr
p Arg Thr Glu Asp Tyr
705                                     7
10                                      7
15                                      7
20

Ser Ser Asp Glu Gln Pro Glu Ser Glu Ser Gl
u Pro Lys Gly
                725
                730
```

What is claimed is:

1. A sperm protein in substantially pure form selected from a human PH30 beta chain protein, a mouse PH30 beta chain protein or an amino acid sequence comprising a disintegrin domain of either the human or mouse PH30 beta chain protein; and wherein the sperm protein has an integrin binding sequence selected from FEE or QDE.

2. The sperm protein of claim 1 which is the human PH30 beta chain protein.

3. The sperm protein of claim 2, having an integrin binding sequence which is FEE.

4. A contraceptive composition comprising a therapeutically effective amount of the protein of claim 1 and a pharmaceutically acceptable carrier.

5. The contraceptive composition of claim 4, wherein the protein is the human PH30 beta chain protein.

6. The composition of claim 4, wherein the protein is produced by expressing a gene encoding the disintegrin domain of the sperm protein in a recombinant DNA expression vector.

7. A method of contraception in a human or mouse subject in need thereof, comprising administering to the subject an amount of the sperm protein of claim 1 which is effective for the stimulation of antibodies which bind to the sperm protein in vivo.

8. An isolated sperm protein made by culturing a transformed host cell which comprises a vector comprising a DNA sequence which encodes a sperm protein selected from a human PH30 beta chain protein as shown in SEQ. I.D. NO. 2 or a mouse PH30 beta chain protein as shown in SEQ. I.D. NO. 4, and isolating the sperm protein.

9. A sperm protein in substantially pure form selected from a human PH30 beta chain protein comprising SEQ. I.D. NO. 2, a segment of the human PH30 beta chain protein comprising amino acid residues 299–392 of SEQ. I.D. NO. 2, a mouse PH30 beta chain protein comprising SEQ. I.D. NO. 4, or a segment of the mouse PH30 beta chain protein comprising amino acid residues 111–202 of SEQ. I.D. NO. 4.

10. The sperm protein of claim 9, selected from the human PH30 beta chain protein comprising SEQ. I.D. NO. 2 or the segment of the human PH30 beta chain protein comprising amino acid residues 299–392 of SEQ. I.D. NO. 2.

11. A contraceptive composition comprising a therapeutically effective amount of the protein of claim 9 and a pharmaceutically acceptable carrier.

12. A method of contraception in a human subject comprising administering to the subject a therapeutically effective amount of the sperm protein of claim 10.

* * * * *